US012709730B2

(12) United States Patent
Le et al.

(10) Patent No.: US 12,709,730 B2
(45) Date of Patent: Aug. 18, 2026

(54) DATA-DRIVEN PREDICTIVE MODELING FOR CELL LINE SELECTION IN BIOPHARMACEUTICAL PRODUCTION

(71) Applicant: AMGEN INC., Thousand Oaks, CA (US)

(72) Inventors: Kim H. Le, Thousand Oaks, CA (US); Yucen Xie, Cambridge, MA (US); Jennitte LeAnn Stevens, Thousand Oaks, CA (US); Aaron Baskerville-Bridges, Cambridge, MA (US)

(73) Assignee: AMGEN INC., Thousand Oaks, CA (US)

( * ) Notice: Subject to any disclaimer, the term of this patent is extended or adjusted under 35 U.S.C. 154(b) by 1167 days.

(21) Appl. No.: 17/607,539

(22) PCT Filed: Apr. 30, 2020

(86) PCT No.: PCT/US2020/030585
§ 371 (c)(1),
(2) Date: Oct. 29, 2021

(87) PCT Pub. No.: WO2020/223422
PCT Pub. Date: Nov. 5, 2020

(65) Prior Publication Data

US 2022/0228102 A1 Jul. 21, 2022

Related U.S. Application Data

(60) Provisional application No. 63/014,398, filed on Apr. 23, 2020, provisional application No. 62/841,186, filed on Apr. 30, 2019.

(51) Int. Cl.

| | |
|---|---|
| ***C12M 1/00*** | (2006.01) |
| ***C12M 1/36*** | (2006.01) |
| ***G16B 40/00*** | (2019.01) |

(52) U.S. Cl.
CPC ............ *C12M 47/04* (2013.01); *C12M 41/48* (2013.01); *G16B 40/00* (2019.02)

(58) Field of Classification Search
CPC ... C12M 41/48; C12M 47/04; G01N 15/1433; G01N 2015/1006; G01N 2015/1486; G16H 50/00; G16H 50/20
See application file for complete search history.

(56) References Cited

U.S. PATENT DOCUMENTS 7,856,321 B2 12/2010 Lanza et al.
9,864,833 B2 1/2018 Fox
(Continued)

FOREIGN PATENT DOCUMENTS

JP 2017511688 A 4/2017
JP 2018503589 A 2/2018
(Continued)

OTHER PUBLICATIONS

Rouiller et al., "A High-throughput Media Design Approach for High Performance Mammalian Fed-batch Cultures", mAbs 5:3, pp. 501-511, May/Jun. 2013.
(Continued)

*Primary Examiner* — Jill A Warden
*Assistant Examiner* — Dwayne K Handy
(74) *Attorney, Agent, or Firm* — MARSHALL, GERSTEIN & BORUN LLP

(57) ABSTRACT

A method for facilitating selection of cell lines to advance to a next stage of cell line screening includes receiving first attribute values for the candidate cell lines measured using an opto-electronic cell line generation and analysis system, and acquiring second attribute values that include one or more attribute values measured at a cell pool screening stage of the candidate cell lines. The method also includes determining a ranking of the candidate cell lines according to a
(Continued)

product quality attribute associated with hypothetical small-scale screening cultures. Determining the ranking includes predicting, for each of the candidate cell lines, a value of the product quality attribute by analyzing the first and second plurality of attribute values using a machine learning based regression estimator, and comparing the predicted values. The method also includes causing an indication of the ranking to be presented to a user via a user interface.

16 Claims, 24 Drawing Sheets

(56) References Cited

U.S. PATENT DOCUMENTS

| | | | |
|---|---|---|---|
| 9,996,920 | B2 | 6/2018 | Du et al. |
| 2012/0185226 | A1 | 7/2012 | Famili et al. |
| 2016/0017319 | A1 | 1/2016 | Nommay et al. |
| 2016/0171686 | A1 | 6/2016 | Du et al. |
| 2017/0258390 | A1 | 9/2017 | Howard |
| 2018/0216100 | A1 | 8/2018 | Serber et al. |

FOREIGN PATENT DOCUMENTS

| | | | |
|---|---|---|---|
| WO | WO-2015113704 | A1 | 8/2015 |
| WO | WO-2016100429 | A1 | 6/2016 |
| WO | WO-2017/100377 | A1 | 6/2017 |

OTHER PUBLICATIONS

Search Report and Written Opinion in International Application No. PCT/US20/30585 dated Oct. 6, 2020, 15 pages.

Japanese Patent Application No. 2021-564140, Notice of Reasons for Rejection, mailed Apr. 9, 2024.

Teixeira et al., High-throughput analysis of animal cell cultures using two-dimensional fluorometry, J. Biotechnol., 151(3):255-60 (Nov. 2010).

European Patent Application No. 20799542.4, Extended European Search Report, dated Jan. 4, 2023.

Japanese Patent Application No. 2024164888, Office Action, mailed Jan. 6, 2026.

Canadian Patent Application No. 3137597, Examiner Report, dated Mar. 13, 2026,.

300

310

| Graph | Input Data | Estimator/Model | Avg $R^2$ | Avg MSE |
|---|---|---|---|---|
| *Top Left* | CLD | *xgboost* | 0.64 | 12.70 |
| *Top Right* | CLD+BD | *xgboost* | 0.93 | 2.81 |
| *Bottom Left* | CLD | Elastic Net | 0.60 | 14.33 |
| *Bottom Right* | CLD+BD | Linear SVM | 0.76 | 8.22 |

| Graph | Input Data | Modality |
|---|---|---|
| *Top Left* | CLD | Bispecific |
| *Top Right* | CLD+BD | Bispecific |
| *Bottom Left* | CLD | mAb |
| *Bottom Right* | CLD+BD | mAb |

| Graph | Input Data | Estimator/Model | Avg $R^2$ | Avg MSE |
|---|---|---|---|---|
| *Top Left* | CLD | *xgboost* | 0.98 | 2.08 |
| *Top Right* | CLD+BD | *xgboost* | 0.98 | 2.26 |
| *Bottom Left* | CLD | Linear SVM | 0.84 | 20.45 |
| *Bottom Right* | CLD+BD | Linear SVM | 0.93 | 8.13 |

| Graph | Input Data | Modality |
|---|---|---|
| *Top Left* | CLD | Bispecific |
| *Top Right* | CLD+BD | Bispecific |
| *Bottom Left* | CLD | mAb |
| *Bottom Right* | CLD+BD | mAb |

Figure 8:
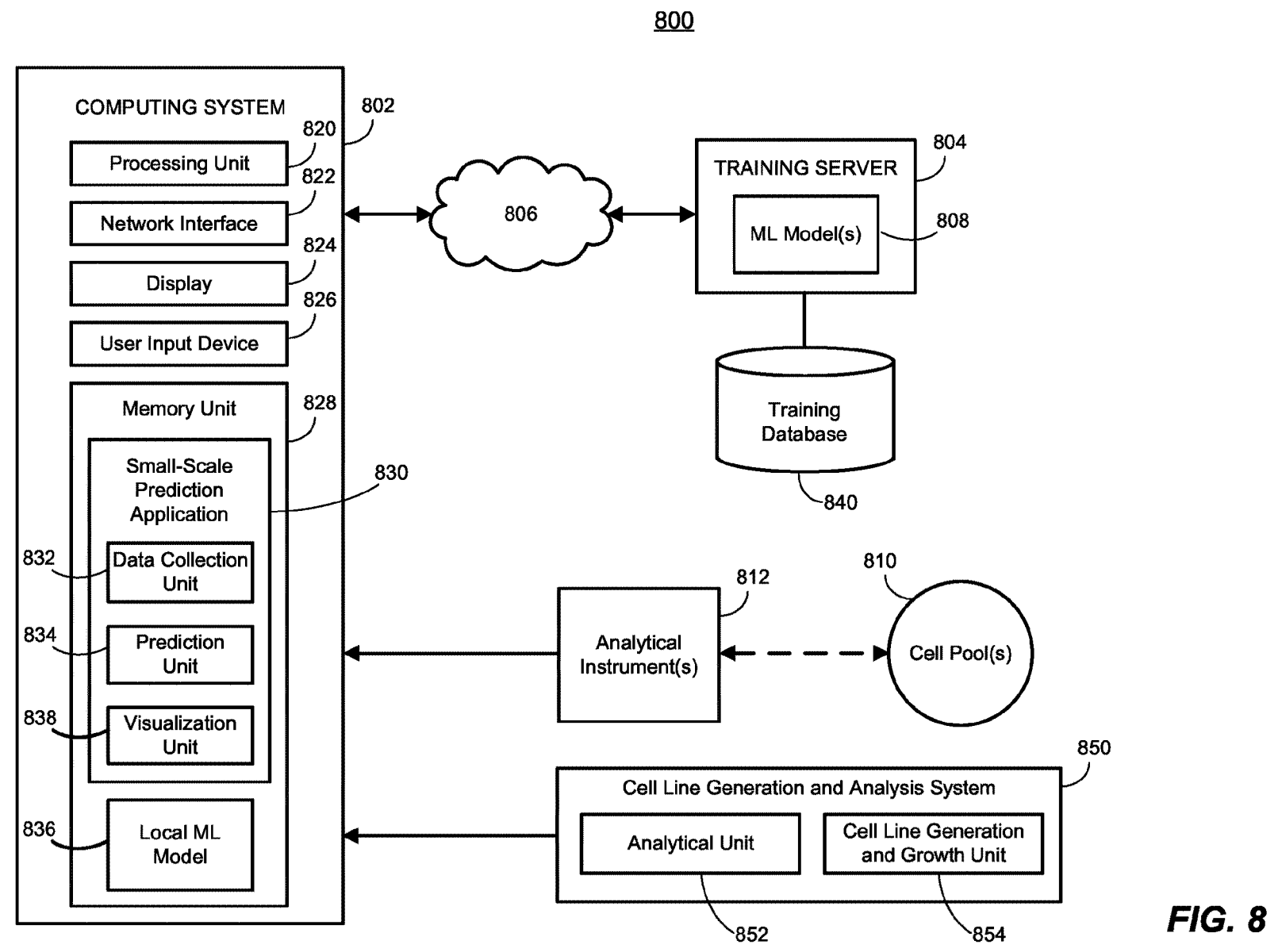

800

COMPUTING SYSTEM 802
Processing Unit 820
Network Interface 822
Display 824
User Input Device 826
Memory Unit 828
Small-Scale Prediction Application 830
Data Collection Unit 832
Prediction Unit 834
Visualization Unit 838
Local ML Model 836

806

TRAINING SERVER 804
ML Model(s) 808
Training Database 840

Cell Pool(s) 810
Analytical Instrument(s) 812

Cell Line Generation and Analysis System 850
Analytical Unit 852
Cell Line Generation and Growth Unit 854

| Model | Train set | Pool_Titer | Spotlight | Cell Count | ... |
|---|---|---|---|---|---|
| Lasso Reg | Cell lines 1,2,3,4,5 | 0.58 | 0.06 | 0 | ... |
| Lasso Reg | Cell lines 1,2,3,4,6 | 0.65 | 0.01 | 0 | ... |
| Lasso Reg | Cell lines 1,2,3,5,6 | 0.72 | 0 | 0 | ... |
| Lasso Reg | Cell lines 1,2,4,5,6 | 0.61 | 0.08 | 0 | ... |
| Lasso Reg | Cell lines 1,3,4,5,6 | 0.68 | 0.06 | 0 | ... |
| Lasso Reg | Cell lines 2,3,4,5,6 | 0.12 | 0.12 | 0 | ... |

932

934
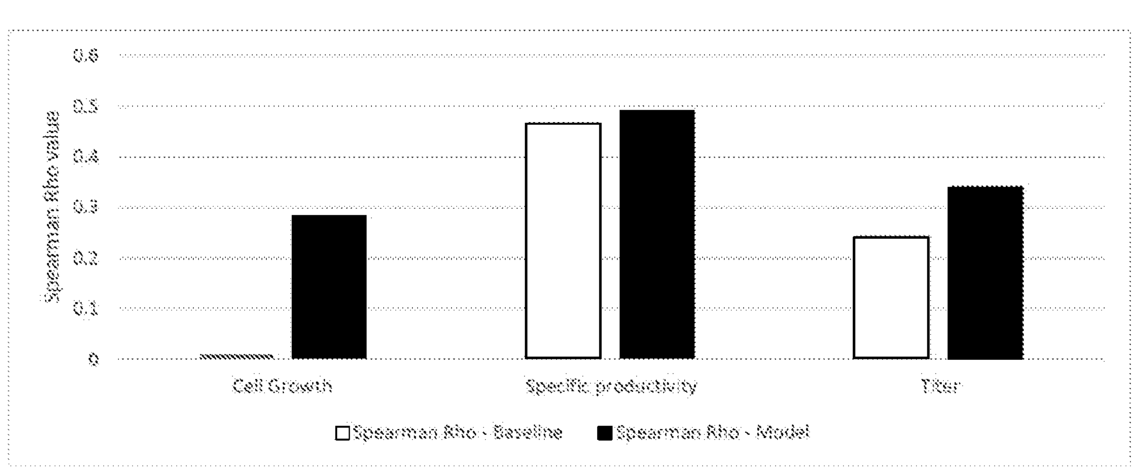
FIG. 12A

936

| Model | Best hyperparameter | Average rho | Average RMSE |
|---|---|---|---|
| **Baseline –** linear regression on Spotlight, Cell Count | N/A | .245 | .668 |
| **Linear regression** | N/A | .340 | .619 |
| **Ridge regression** | **Lambda=1.3** | **.341** | **.616** |
| **Lasso regression** | Lambda=0.001 | .340 | .621 |
| **PCA** | Score = 2 | .340 | .619 |
| **PLS** | Score = 2 | .340 | .619 |
| **Random Forest** | Min leaf size = 4 | .211 | .674 |
| **XGBoost** | Learn rate = 0.5 | .016 | .736 |

| Spotlight | Pool Titer |
|---|---|
| 0.116293 | 0.593201 |

| **Model** | **Best hyperparameter** | **Average rho** | **Average RMSE** |
|---|---|---|---|
| **Linear regression** | N/A | .467 | 17.6 |
| **Ridge regression** | Lambda=9 | .319 | 11.75 |
| **Lasso regression** | Lambda=0.19 | .449 | 13.67 |
| **PCA** | **Score = 2** | **.492** | **12.80** |
| **PLS** | Score = 2 | .459 | 11.69 |
| **Random Forest** | Min leaf size = 3 | .328 | 15.15 |
| **XGBoost** | Learn rate = 0.35 | .226 | 15.05 |

| Component | Pool_Titer | Adj_Au | Pool_qP | Pool_VCD_D06 | QP_BLI_adj | Scaled_Au | Au_x_CC_Scaled | Au_Scaled^2 |
|---|---|---|---|---|---|---|---|---|
| 1 | 0.42 | 0.47 | 0.09 | -0.23 | 0.43 | 0.41 | 0.06 | 0.40 |
| 2 | -0.27 | -0.13 | -0.24 | 0.20 | -0.17 | 0.39 | 0.65 | 0.34 |

| Model | Best hyperparameter | Average rho | Average RMSE |
| --- | --- | --- | --- |
| **Linear regression** | N/A | .001 | 42.4 |
| **Ridge regression** | Lambda=8 | .206 | 51.5 |
| **Lasso regression** | Lambda=0.19 | .219 | 51.2 |
| **PCA** | Score = 2 | .220 | 54.5 |
| **PLS** | **Score = 1** | **.283** | **49.1** |
| **Random Forest** | Min leaf size = 2 | .066 | 56.9 |
| **XGBoost** | Learn rate = 0.2 | .098 | 58.9 |

| Cell Count | Pool_VIA_D06 | Pool_VIA_D08 | Pool_VIA_D10 | Pool_IVCD | Pool_VCD_D06 | Pool_VCD_D08 | Pool_VCD_D10 | Pool_Titer |
| --- | --- | --- | --- | --- | --- | --- | --- | --- |
| -0.08 | 0.18 | 0.16 | 0.18 | 0.27 | 0.24 | 0.21 | 0.02 | 0.45 |

*FIG. 12G*

DATA-DRIVEN PREDICTIVE MODELING FOR CELL LINE SELECTION IN BIOPHARMACEUTICAL PRODUCTION

CROSS-REFERENCE TO RELATED APPLICATIONS

Priority is claimed to U.S. Provisional Patent Application No. 62/841,186, filed Apr. 30, 2019, and to U.S. Provisional Patent Application No. 63/014,398, filed Apr. 23, 2020, the entire disclosures of which are hereby incorporated herein by reference.

FIELD OF DISCLOSURE

The present application relates generally to cell line (clone) selection techniques, and more specifically relates to techniques for predicting a relative rank of cell lines advanced from a clone generation and analysis process, according to a certain product quality attribute.

BACKGROUND

In the biopharmaceutical industry, large, complex molecules (e.g., proteins) known as biologics are derived from living systems. The general workflow for the development of a biologic begins with research and development. In this initial phase, a disease, or indication, that represents an important unmet medical need is targeted. Researchers determine the potential drug candidates based on a proper target product profile, which govern aspects such as safety, efficacy, and route of administration, for example. Ultimately, through a combination of in vitro research and computational models, a specific molecule is chosen as the top drug candidate for the specific disease and target population. After the top candidate is selected, the blueprint for the molecule is formalized into a gene, and the gene of interest is inserted into an expression vector. The expression vector is then inserted into the host cell, in a process known as transfection. The cell can incorporate the gene of interest into its own production mechanisms upon successful transfection, eventually gaining the ability to produce the desired pharmaceutical product.

Because each cell has unique characteristics, the product produced by each cell varies slightly, e.g., in terms of productivity (e.g., titer) and product quality. In general, it is more desirable to produce drugs with consistently high titers and consistently high quality, for reasons of economy and safety. High concentrations, or titers, of a product help to reduce the manufacturing footprint needed to generate desired production volumes, and therefore save both capital and operating expenses. High product quality ensures that a greater proportion of the drug is safe, efficacious, and usable, which also saves costs. In the context of cell line development, product quality attributes are evaluated through assays conducted on the product of interest. These assays often include chromatographic analysis, which is used to determine attributes such as degree of glycosylation and other factors such as the proportion of unusable proteins due to truncations (clippings) or clumping (aggregates).

Based on criteria relating to productivity and product quality, the "best" cell line or clone is selected in a process known as "cell line selection," "clone selection," or "clone screening." The selected cell line/clone is used for the master cell bank, which serves as the homogeneous starting point for all future manufacturing (e.g., clinical and commercial).

Ensuring a consistent product batch helps promote a more uniform and predictable pharmacokinetic and pharmacodynamic response in patients. If a "pool" of heterogeneous cells obtained after transfection is used to generate the product of interest, however, there may be many variants of the product generated. This is because during transfection, the gene of interest is integrated into candidate host cells in variable ways. For example, there may be differences in copy number (i.e., the number of integrated copies of the gene of interest) and other differentiating factors between the unique footprints of different cells. The manufacturing of the product of interest may also vary due to slight differences in the internal machinery of each individual cell, including the nature of post-translational modifications. These variations are undesirable, especially considering the need to ultimately control for and ensure a measured and safe response in the patient. Thus, it is typically required that the master cell bank cell line be "clonally derived," i.e., that the master cell bank only contain cells derived from a common, single cell ancestor. This theoretically helps ensure a large degree of homogeneity in the drug produced, despite slight, inevitable differences due to natural genetic variation through random mutation as cells divide. Therefore, the clone screening process is important in delivering not only a productive, high quality starting material, but also a singular cell line that complies with the "clonally derived" requirement.

FIG. 1 depicts a typical clone screening process 10. The first stage 11 depicts the traditional microtiter plate-based method of clone generation and growth, which may take two to three weeks. Hundreds of pooled, heterogeneous cells are sorted into single-cell cultures through processes such as fluorescence-activated cell sorting (FACS) or limiting dilution. After being allowed to recover to healthy and stable populations, these clonally-derived cells are analyzed, and select populations are transferred to stage 12. At stage 12, clone cells in small containers, such as spin tubes, 24-well plates, or 96-deep well plates are cultured in a "small-scale cell culture" (e.g., a 10-day fed batch process). In this small-scale process, boluses of nutrients are added periodically, and different measurements of cell growth and viability are obtained. Typically, hundreds or even thousands of these small-scale cultures are run in parallel. At the end of the culture (e.g., the tenth day), the cells are harvested for assays and analysis.

By analyzing the growth and productivity characteristics of the clones in the small-scale cultures, at stage 12, the "top" or "best" clones (e.g., the top four) are selected for scaled-up cultures that are run at a third stage 14. The scaled-up (or "large-scale") process is useful because, relative to the small-scale cultures at stage 12, it better represents the process that will ultimately be used in clinical and commercial manufacturing. The scaled-up process may occur through a 15-day culture in 3 to 5 liter perfusion bioreactors, for example. These perfusion bioreactors accommodate more efficient transfer of waste and nutrients, thereby increasing overall productivity of the culture. Perfusion bioreactors are also typically associated with a higher number of measured variables, such as daily and continuous process conditions and metabolite concentrations, to enable tighter control and monitoring.

After the scaled-up process at stage 14, the media and product are collected and analyzed. Ultimately, at a fourth stage 16, the scaled-up run that yielded the highest titer and exhibited the best product quality attributes (PQA) is typically chosen as the "best," or "winning," clone. Finally, at a fifth stage 18, the winning clone is used as the master cell bank for future clinical and commercial manufacturing use.

Conventional clone screening processes of the sort described above are extremely resource-intensive, typically taking several months and requiring hundreds or thousands of assays and cell cultures. As the pace of biotechnology quickens, however, and as an increased emphasis is placed on processing additional molecules in the early-stage pipeline, there is an increasing need for faster clone screening. Moreover, conventional clone screening processes lack standardized criteria for selecting which clones to advance to the next stage/bioprocess and, ultimately, selecting a winning clone, in part because the unique combination of modality, structure, and sequence characteristics for each different drug candidate means that different factors can be more or less important.

SUMMARY

Embodiments described herein relate to systems and methods that create, evaluate, and/or apply predictive models of cell line and bioprocess performance in clone selection. In particular, robust machine learning models are created, and used to reduce development timelines and resource usage while improving performance.

In one aspect, one or more machine learning algorithms can be used to predict performance of each and every clone in a hypothetical, scaled-up (bioreactor) culture, based on measurements and other data pertaining to real-world, small-scale cultures of those same clones. While large-scale culture performance may be predicted for a hypothetical/virtual culture spanning days (e.g., a 15-day culture), each prediction can be made almost instantly. Depending on the embodiment, this process may result in selecting better clones/cell lines for scaled-up experiments (i.e., clones that are more likely to perform well in large-scale cultures), or may even result in selecting a "winning" clone without running any scaled-up experiments whatsoever (e.g., by selecting the clone that has the best predicted bioreactor performance), which may cut a month or more off of the critical path for a biologics program.

Using the predictive models described herein, a higher-producing and/or better quality clone may be identified relative to the conventional "funnel" approach (i.e., proceeding from stage 12 to stage 14 to stage 16 in FIG. 1). This improvement occurs because small-scale results, despite some similarities, are not completely representative of scaled-up results. In other words, merely selecting the clones with the best productivity and/or product quality at stage 12, according to some predefined criteria, does not necessarily result in the best productivity and/or product quality (according to the same criteria) at stage 14.

Furthermore, interpretable machine learning algorithms may be used to identify the input features (e.g., small-scale culture measurements) that are most important to generating accurate predictions. This can be helpful when considering that in any given clone screening program, a very large number of attributes (e.g., over 600) may be tracked. Thus, for example, it may be possible to make sufficiently accurate predictions using a relatively small number of input features (e.g., about 10 features), and eliminating the need to measure numerous other attributes. Knowledge of the correlations between measurements and desired prediction targets can also provide scientific insight, and spawn hypotheses for further investigation that can lead to future bioprocess improvements.

In another aspect, in addition to or instead of the process described above, one or more machine learning algorithms can be used to select which clones should advance from the subcloning stage to small-scale screening cultures (e.g., from stage 11 to stage 12 of FIG. 1). Typically, clones that have both high cell productivity scores and high cell counts at the end of the subcloning stage have been considered to be the best candidates to achieve high performance in small-scale screening cultures (fedbatch experiments). This approach typically results in the advancement of roughly 30 to 100 clones to the fedbatch stage. Machine learning algorithms described herein can improve on this process, however, by analyzing various attributes of candidate clones, both at the subcloning stage and the preceding cell pool stage, to predict a particular product quality attribute (e.g., titer, cell growth, or specific productivity) that would result from hypothetical small-scale (e.g., fedbatch) culture experiments. The microtiter plate-based method of clone generation and growth (i.e., subcloning stage 11 in FIG. 1) may be substituted with the use of a more efficient, high-throughput and high-content screening tool, such as the Berkeley Lights Beacon™ opto-electronic cell line generation and analysis system, for example. After predicting product quality attribute values for the candidate cell lines, the candidates are ranked according to the predicted values, thereby facilitating the selection of a smaller subset of the candidate clones to the next stage of cell line development. Advantageously, rankings formed according to these values can be highly accurate with certain machine learning models, even if the underlying predicted values exhibit relatively low accuracy and thus would on the surface appear to be insufficient. Depending on the embodiment, this process may require less resource usage (e.g., in terms of time, cost, labor, equipment, etc.), and/or provide better standardization, when selecting candidate clones/cell lines for small-scale screening cultures (i.e., clones that are more likely to be the best performers in small-scale cultures). For example, reducing the number of cells advanced to the fedbatch stage could free up capacity to test other cell lines for other drug products. In some embodiments, the small-scale screening stage may be skipped entirely (e.g., by passing straight from stage 11 to stage 14 of process 10), based on the rankings for the various cell lines.

BRIEF DESCRIPTION OF THE DRAWINGS

The skilled artisan will understand that the figures, described herein, are included for purposes of illustration and do not limit the present disclosure. The drawings are not necessarily to scale, and emphasis is instead placed upon illustrating the principles of the present disclosure. It is to be understood that, in some instances, various aspects of the described implementations may be shown exaggerated or enlarged to facilitate an understanding of the described implementations. In the drawings, like reference characters throughout the various drawings generally refer to functionally similar and/or structurally similar components.

FIG. 8 is a simplified block diagram of an example system that may implement the techniques of a second aspect of the invention described herein.

FIGS. 12A trough 12G depict observed model performance and/or feature importance for various models and target product quality attributes.

DETAILED DESCRIPTION

The various concepts introduced above and discussed in greater detail below may be implemented in any of numerous ways, and the described concepts are not limited to any particular manner of implementation. Examples of implementations are provided for illustrative purposes.

Figure 2:
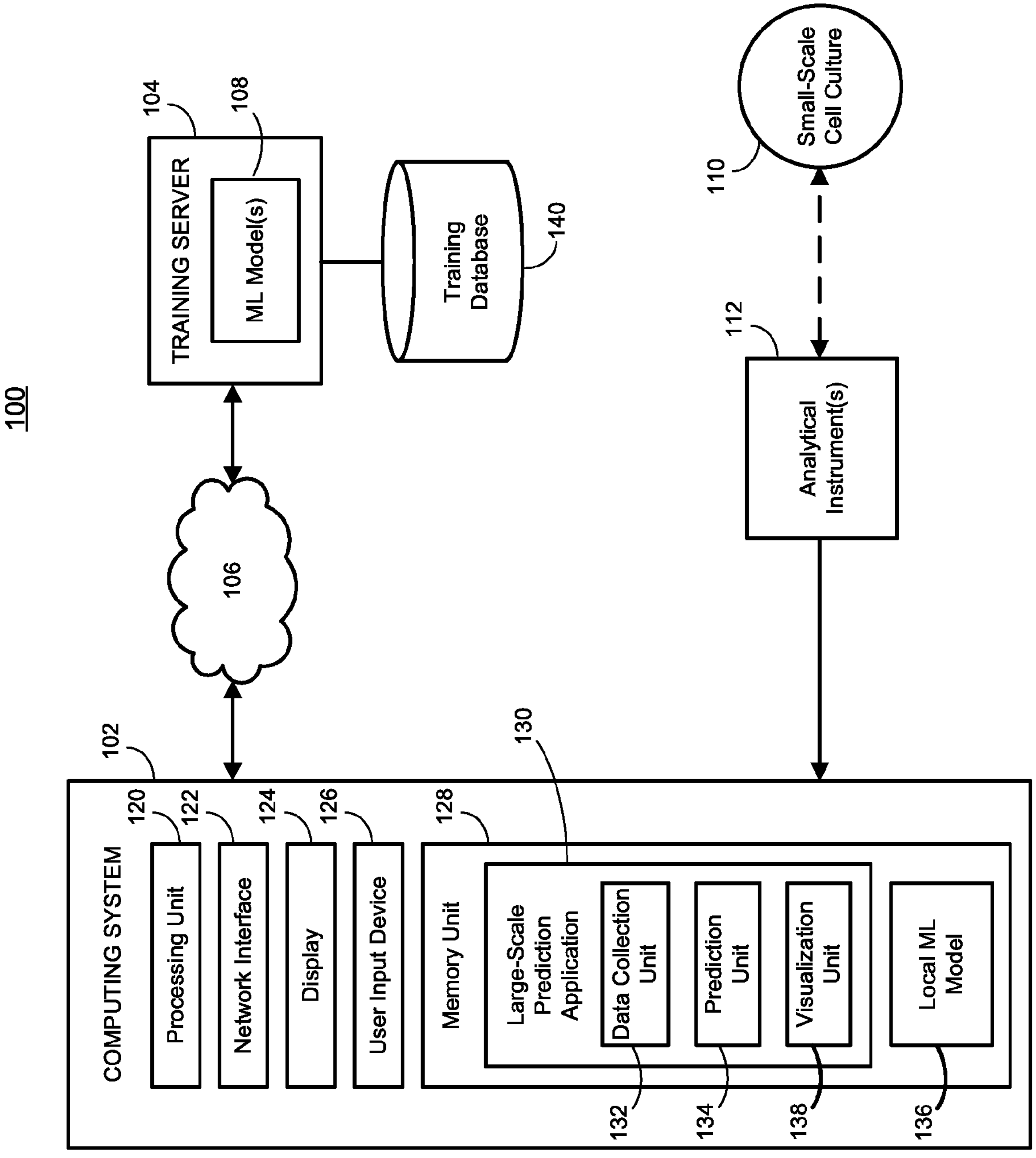
FIG. 2 is a simplified block diagram of an example system that may implement the techniques of a first aspect of the invention described herein.

FIG. 2 is a simplified block diagram of an example system 100 that may implement the techniques of the first aspect described herein. System 100 includes a computing system 102 communicatively coupled to a training server 104 via a network 106. Generally, computing system 102 is configured to predict large-scale (bioreactor) cell culture performance of specific cell lines (e.g., productivity and/or product quality attributes) based on small-scale culture measurements for those cell lines, and possibly also based on other parameters (e.g., modality), using one or more machine learning (ML) models 108 trained by training server 104.

Network 106 may be a single communication network, or may include multiple communication networks of one or more types (e.g., one or more wired and/or wireless local area networks (LANs), and/or one or more wired and/or wireless wide area networks (WANs) such as the Internet). In various embodiments, training server 104 may train and/or utilize ML model(s) 108 as a "cloud" service (e.g., Amazon Web Services), or training server 104 may be a local server. In the depicted embodiment, however, ML model(s) 108 is/are trained by server 104, and then transferred to computing system 102 via network 106 as needed. In other embodiments, one, some or all of ML model(s) 108 may be trained on computing system 102, and then uploaded to server 104. In still other embodiments, computing system 102 trains and maintains/stores the model(s) 108, in which case system 100 may omit both network 106 and training server 104.

FIG. 2 depicts a scenario in which computing system 102 makes predictions based on measurements of a specific, small-scale cell culture 110. Culture 110 may be a culture of a specific cell line (e.g., from Chinese hamster ovary (CHO) cells) within a single container, such as a well or vial, for example. The cell line of culture 110 may be any suitable cell line that produces recombinant proteins, and of any particular modality. The cell line may be a monoclonal antibody (mAb) producing cell line, or a cell line that produces a bispecific or other multispecific antibody, for example. It will also be appreciated that computing system 102 may make predictions based on measurements of cells cultured in a microfluidic environment, such as in an opto-electronic instrument as described herein.

One or more analytical instruments 112 are configured, collectively, to obtain the physical measurements that will be used by computing system 102 to make predictions, as discussed further below. Analytical instrument(s) 112 may obtain the measurements directly, and/or may obtain or facilitate indirect or "soft" sensor measurements. As used herein, the term "measurement" may refer to a value that is directly measured/sensed by an analytical instrument (e.g., one of instrument(s) 112), a value that an analytical instrument computes based on one or more direct measurements, or a value that another device (e.g., computing system 102) computes based on one or more direct measurements. Analytical instrument(s) 112 may include instruments that are fully automated, and/or instruments that require human assistance. As just one example, analytical instrument(s) 112 may include one or more chromatograph devices (e.g., devices configured to perform size exclusion chromatography (SEC), cation exchange chromatography (CEX), and/or hydrophilic-interaction chromatography (HILIC)), one or more devices configured to obtain measurements for determining titer for a target product, one or more devices configured to directly or indirectly measure metabolite concentrations of the culture medium (e.g., glucose, glutamine, etc.), and so on.

Computing system 102 may be a general-purpose computer that is specifically programmed to perform the operations discussed herein, or may be a special-purpose computing device. As seen in FIG. 2, computing system 102 includes a processing unit 120, a network interface 122, a display 124, a user input device 126, and a memory unit 128. In some embodiments, however, computing system 102 includes two or more computers that are either co-located or remote from each other. In these distributed embodiments, the operations described herein relating to processing unit 120, network interface 122 and/or memory unit 128 may be divided among multiple processing units, network interfaces and/or memory units, respectively.

Processing unit 120 includes one or more processors, each of which may be a programmable microprocessor that executes software instructions stored in memory unit 128 to execute some or all of the functions of computing system 102 as described herein. Processing unit 120 may include one or more central processing units (CPUs) and/or one or more graphics processing units (GPUs), for example. Alternatively, or in addition, some of the processors in processing unit 120 may be other types of processors (e.g., application-specific integrated circuits (ASICs), field-programmable gate arrays (FPGAs), etc.), and some of the functionality of computing system 102 as described herein may instead be implemented in hardware. Network interface 122 may include any suitable hardware (e.g., a front-end transmitter and receiver hardware), firmware, and/or software configured to communicate with training server 104 via network 106 using one or more communication protocols. For example, network interface 122 may be or include an Ethernet interface, enabling computing system 102 to communicate with training server 104 over the Internet or an intranet, etc.

Display 124 may use any suitable display technology (e.g., LED, OLED, LCD, etc.) to present information to a user, and user input device 126 may be a keyboard or other suitable input device. In some embodiments, display 124 and user input device 126 are integrated within a single device (e.g., a touchscreen display). Generally, display 124 and user input device 126 may combine to enable a user to interact with graphical user interfaces (GUIs) provided by computing system 102, e.g., as discussed below with reference to FIGS. 6A and 6B. In some embodiments, however, computing system 102 does not include display 124 and/or user input device 126, or one or both of display 124 and user input device 126 is/are included in another computer or system (e.g., a client device) that is communicatively coupled to computing system 102.

Memory unit 128 may include one or more volatile and/or non-volatile memories. Any suitable memory type or types may be included, such as read-only memory (ROM), random access memory (RAM), flash memory, a solid-state drive (SSD), a hard disk drive (HDD), and so on. Collectively, memory unit 128 may store one or more software applications, the data received/used by those applications, and the data output/generated by those applications. These applications include a large-scale prediction application 130 that, when executed by processing unit 120, predicts performance (e.g., productivity and/or product quality attributes) of a specific cell line in a virtual/hypothetical large-scale culture based on the small-scale measurements obtained by analytical instrument(s) 112 (and possibly also based on other information, such as modality). While various modules of application 130 are discussed below, it is understood that those modules may be distributed among different software applications, and/or that the functionality of any one such module may be divided among two or more software applications.

A data collection unit 132 of application 130 collects values of various attributes associated with small-scale cell cultures, such as culture 110. For example, data collection unit 132 may receive measurements directly from analytical instrument(s) 112. Additionally or alternatively, data collection unit 132 may receive information stored in a measurement database (not shown in FIG. 2) and/or information entered by a user (e.g., via user input device 126). For example, data collection unit 132 may receive a modality, target drug product, drug protein scaffold type, and/or any other suitable information entered by a user and/or stored in a database. Additionally or alternatively, data collection unit may receive measurements from an opto-electronic device as described herein.

For a given small-scale cell culture corresponding to a specific cell line, a prediction unit 134 of application 130 operates on the attribute values collected by data collection unit 132 to output one or more predicted attribute values corresponding to a hypothetical/virtual large-scale culture, using a local machine learning model 136. That is, the attribute values collected by data collection unit 132 are used as inputs/features for machine learning model 136. The attribute(s) for which value(s) is/are predicted may include one or more productivity metrics (e.g., titer) and/or one or more product quality metrics (e.g., SEC main peak, low molecular weight peak, and/or high molecular weight peak percentage(s)). In the depicted embodiment, machine learning model 136 is a local copy of one of the model(s) 108 trained by training server 104, and may be stored in a RAM of memory unit 128, for example. As noted above, however, server 104 may utilize all models 108 in other embodiments, in which case no local copy need be present in memory unit 128.

A visualization unit 138 of application 130 generates a user interface that enables users to enter information indicative of a use case (e.g., which large-scale attribute value(s) to predict, modality, etc.) via user input device 126, and enables users to observe visual representations of the prediction(s) made by prediction unit 134 (and/or other information derived therefrom) via display 124. Screenshots of an example user interface that may be generated by visualization unit 138 are discussed below with reference to FIGS. 6A and 6B.

Operation of system 100, according to one embodiment, will now be described in further detail, for the specific scenario in which application 130 is used to predict large-scale performance for a number of different cell lines (clones) in small-scale cultures, including the specific cell line of small-scale cell culture 110. By so doing, a better selection of cell lines may be identified for scale-up (e.g., for stage 14 of process 10 in FIG. 1), or the scale-up stage may be skipped entirely (e.g., by passing straight from stage 12 to stage 16 of process 10, based on the predictions for the various cell lines).

Initially, training server 104 trains machine learning model(s) 108 using data stored in a training database 140. Machine learning model(s) 108 may include a number of different types of machine learning based regression estimators (e.g., a decision tree regressor model, a random forest regressor model, a linear support vector regression model, an eXtreme gradient boosting (xgboost) regressor model, etc.), and possibly also one or more models not based on regression (e.g., a neural network). Moreover, model(s) 108 may include more than one model of any given type (e.g., two or more models of the same type that are trained on different historical datasets and/or using different feature sets), in some embodiments. Furthermore, different models of models 108 may be trained to predict different large-scale culture attribute values (e.g., titer, or a chromatography SEC value, etc.). As discussed further below with reference to FIGS. 4A and 4B, each of machine learning models 108 may be optimized (trained and tuned) for a specific use case, or for a specific class of use cases. Moreover, as discussed further below with reference to FIGS. 5A through 5D, each of machine learning models 108 may be used to identify which features (e.g., small-scale culture attribute values) are most predictive of a particular large-scale culture attribute value, and/or may be trained or re-trained using a feature set that only includes the features that are most predictive of a particular large-scale culture attribute value.

Training database 140 may include a single database stored in a single memory (e.g., HDD, SSD, etc.), or may include multiple databases stored in one or more memories. For each different model within machine learning model(s) 108, training database 140 may store a corresponding set of training data (e.g., input/feature data, and corresponding labels), with possible overlap between the training data sets. To train a model that predicts titer, for instance, training database 140 may include numerous feature sets each comprising historical small-scale culture measurements that were made by one or more analytical instruments (e.g., analytical instrument(s) 112 and/or similar instruments), and possibly other information (e.g., modality), along with a label for each feature set. In this example, the label for each feature set indicates the large-scale culture titer value (e.g., end-point titer at Day 15) that was measured when the cell line of the small-scale culture was scaled-up in a bioreactor. In some embodiments, all features and labels are numerical, with non-numerical classifications or categories being mapped to numerical values (e.g., with the allowable values [Bispecific Format 1, Bispecific Format 2, Bispecific Format 1 or 2] of a modality feature/input being mapped to the values [10, 01, 00]).

In some embodiments, training server 104 uses additional labeled data sets in training database 140 in order to validate the trained machine learning model(s) 108 (e.g., to confirm that a given one of machine learning model(s) 108 provides at least some minimum acceptable accuracy). Validation of model(s) 108 is discussed further below with reference to FIG. 3. In some embodiments, training server 104 also updates/refines one or more of machine learning model(s) 108 on an ongoing basis. For example, after machine learning model(s) 108 is/are initially trained to provide a sufficient level of accuracy, additional measurements at both small-scale (features) and large-scale (labels) may be used to improve prediction accuracy.

Application 130 may retrieve, from training server 104 via network 106 and network interface 122, a specific one of machine learning models 108 that corresponds to a use case of interest. The use case may be one that was indicated by a user via a user interface, for example (e.g., as discussed below with reference to FIG. 6A). Upon retrieving the model, computing system 102 stores a local copy as local machine learning model 136. In other embodiments, as noted above, no model is retrieved, and input/feature data is instead sent to training server 104 (or another server) as needed to use the appropriate model of model(s) 108.

In accordance with the feature set used by model 136, data collection unit 132 collects the necessary data. For example, data collection unit 132 may communicate with analytical instrument(s) 112 to collect measurements of titer, chromatography values, metabolite concentrations, and/or other specific attributes of small-scale cell culture 110. In one such embodiment, data collection unit 132 sends commands to one or more of analytical instrument(s) 112 to cause the one or more instruments to automatically collect the desired measurements. In another embodiment, data collection unit 132 collects the measurements of small-scale cell culture 110 by communicating with a different computing system (not shown in FIG. 2) that is coupled to (and possibly controls) analytical instrument(s) 112. As noted above, data collection unit 132 may also receive information entered by a user (e.g., modality, target drug product, etc.). In some embodiments, some user-entered information collected by data collection unit 132 is used to select an appropriate one of models 108, while other user-entered information collected by data collection unit 132 is used as (or used to derive) one or more features/inputs to the selected model.

After data collection unit 132 has collected the attribute values that are associated with small-scale cell culture 110 (and possibly other data, such as target drug product, etc.), and that are used as inputs/features by local machine learning model 136, prediction unit 134 causes model 136 to operate on those inputs/features to output a prediction of one or more large-scale cell culture attribute values for the same cell line. It is understood that, in some embodiments and/or scenarios, local machine learning model 136 may include two or more models that each predict/output a different large-scale culture attribute value.

The large-scale culture attribute value(s) output by model 136 may include values of, for example, one or more productivity attributes such as titer or viable cell density (VCD), and/or one or more product quality attributes such as SEC main peak (MP) percentage, SEC low molecular weight (LMW) peak percentage, and/or SEC high molecular weight (HMW) peak percentage. Visualization unit 138 causes a user interface, depicted on display 124, to present the predicted attribute value(s), and/or other information derived from the predicted attribute value(s). For example, visualization unit 138 may cause the user interface to present an indication of whether the predicted attribute value(s) satisfy one or more cell line selection criteria (e.g., after application 130 compares the attribute value(s) to one or more respective threshold values).

The above process may be repeated for a number of different cell lines, each of which is used for a small-scale cell culture similar to small-scale cell culture 110. For example, computing system 102 (or another computing system not shown in FIG. 2) may cause analytical instrument(s) 112 to sequentially obtain measurements from hundreds or thousands of small-scale cell cultures, each containing a different clone/cell line, and prediction unit 134 may cause model 136 to operate on each set of measurements (and possibly other data) to output a respective large-scale prediction or set of predictions.

Prediction unit 134 may store the predictions made by model 136 for each cell line, and/or information derived from each prediction set, in memory unit 128 or another suitable memory/location. After predictions have been made and stored for all cell lines under consideration, a "winning" cell line may be selected (e.g., similar to stage 16 of FIG. 1). The selection of a winning cell line may be fully automated according to some criteria specific to the use case (e.g., by assigning specific weights to productivity and product quality attributes and then comparing scores), or may involve human interaction (e.g., by simply displaying the predicted large-scale attribute values to a user via display 124). Alternatively, after predictions have been made and stored for all cell lines under consideration, a subset of the cell lines may be selected for scale-up (e.g., similar to stage 14 of FIG. 1). Again, this selection may be fully automated according to some criteria specific to the use case, or may involve human interaction.

As noted above, training server 104 may train a number of different predictive models 108 that are particularly well-suited to specific use cases, or to specific classes of use cases. Moreover, to avoid the time and cost of having to perform and collect a very large number of small-scale analytical measurements (and possibly other information), interpretable machine learning models may be used. For example, training server 104 may train one of models 108 on hundreds of features (e.g., ~600 features), after which training server 104 (or a human reviewer) may analyze the trained model (e.g., weights assigned to each feature) to determine the most predictive features (e.g., ~10 features). Thereafter, that particular model, or a new version of that model that has been trained using only the most predictive features, may be used with a much smaller feature set. Identifying highly predictive features may also be useful for other purposes, such as providing new scientific insights that may give rise to new hypotheses, which could in turn lead to bioprocess improvements.

Various techniques for determining which models are best suited for particular use cases, and for identifying the most predictive features for a given model or use case, are now described with reference to FIGS. 3 through 5.

Generally, well-performing models for specific use cases may be identified by training a number of different models using historical training data generated from previous clone screening runs, and comparing the results. The historical data may include small-scale cell line development data (e.g., small-scale fed batch measurement data) as well as scaled-up bioreactor data (e.g., perfusion bioreactor measurements). Moreover, the historical data may include both categorical data, such as media type and modality, and numerical data, such as metabolite concentrations and titer values. For small-scale cell line development data (also referred to herein as simply "cell line development data" or "CLD data"), growth factors such as viability, VCD and glucose concentrations may be collected periodically over time (e.g., at different days of a 10-day culture). For scaled-up bioreactor data (also referred to herein as "bioprocess development data" or "BD data"), these attributes, and possibly additional attributes such as pH level and dissolved oxygen concentration, may be collected and recorded in connection with each feature set. The bioreactor data may also include data that serves as the labels for the various feature sets, such as product titers and other analytic results from assays (e.g., results of SEC and/or CEX analysis). Various measures may be taken to ensure a robust set of training data (e.g., providing standardized, heterogeneous data, removing outliers, imputing missing values, and so on).

In some embodiments, special feature engineering techniques are used to extract or derive useful features. For example, a convolutional neural network (or an API that automatically extracts summary statistics from temporal data, such as tsfresh) may be used to detect temporal dependencies among various attributes (e.g., a high correlation between VCD at Day 0 of the small-scale culture and VCD at Day 6 of the small-scale culture, etc.). These temporal dependencies may be used to extract/derive useful features for model training. Other feature engineering techniques may also be used, such as variance thresholding, principal component analysis (PCA), mutual information regression, analysis of variance (ANOVA), and eliminating features with high covariance, for example.

For any supervised machine learning regression model generated using the historical training data, the task is to find a function $f$ that best maps the input/feature data x to a prediction $\hat{y}$. This mapping should minimize the error e between the prediction $\hat{y}$ and future data y*, as represented in the following equation:

$$f(x)=\hat{y} \text{ s.t. } \min_{e} y^{*}=f(x)+e \quad \text{(Equation 1)}$$

Furthermore, minimizing this model error against historical training data is insufficient. Ideally, the model should be accurate when it is exposed to new data. In this manner, machine learning algorithms may be constructed that take in data from earlier experiments to generate predictions of end results for new experiments/programs.

Figure 3:
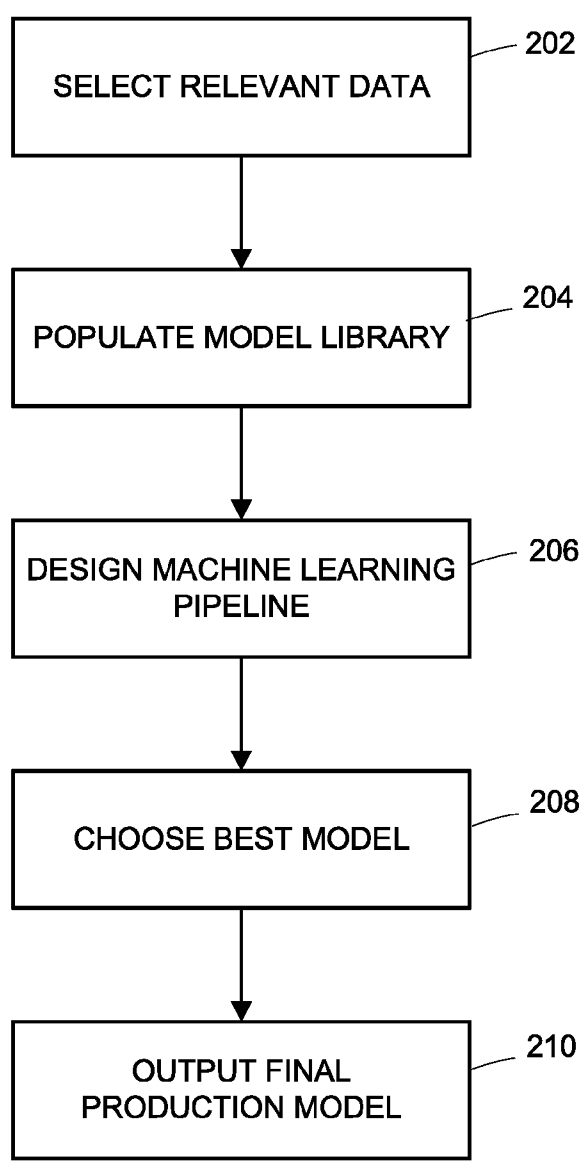
FIG. 3 is a flow diagram of an example process for generating a machine learning model specific to a particular use case.

A modular, flexible process 200 that can be used as a framework for identifying well-performing models for each of a number of different use cases is shown in FIG. 3. Initially, at stage 202, relevant data corresponding to a given use case is selected from among available historical data. A "use case" may be defined in various ways, in a manner that determines which data is relevant to that use case. For example, a use case may be defined as a specific target variable (y), a specific modality or set of modalities, and possibly one or more specific limitations on the feature dataset. As a more specific example, a use case may correspond to (1) end-point titer for a large-scale culture (bioreactor) as the target variable, (2) all modalities (e.g., monoclonal antibodies, and bispecific or multispecific formats that can be considered), and (3) only using historical cell line development data as (and/or to derive) features of the training data. Conversely, another use case may correspond to (1) chromatography analysis results (e.g., SEC main peak) for a large-scale culture as the target variable, (2) only a single modality (e.g., a particular monoclonal antibody, or bispecific or multispecific antibody format), and (3) using both historical cell line development data and historical bioreactor data as (and/or to derive) features of the training data.

At stage 204, a model library for the use case is populated. Stage 204 includes selection of a number of candidate machine learning models/estimators that may or may not turn out to be particularly well-suited to predicting the target attribute value for the use case. In order to yield accurate and interpretable results, some or all of the machine learning models selected at stage 204 should meet two criteria. First, machine learning models that can assign weights to input features are preferred, as such models can explain the relative importance of each input feature with respect to predicting the target output. Second, sparsity-inducing machine learning models are preferred (e.g., a model that initially accepts many attribute values as features, but only requires a small subset of those attribute values as features to make accurate predictions). This property mitigates overfitting while also improving interpretability by excluding features that do not significantly affect the target result. Sparsity-inducing models can also save time and cost, by removing the need to measure the excluded attribute values. Regression models/estimators based on decision trees (e.g., decision/ID tree models, random forest models, xgboost models, gradient boosting models, etc.), or based on other machine learning algorithms (e.g., support vector machines (SVM) with linear basis and/or radial basis function kernels, elastic net, etc.), can be particularly well-suited to satisfying both criteria noted above. While not traditionally viewed as being interpretable, one or more neural networks may also be selected at stage 204, in some embodiments.

At stage 206, a machine learning pipeline is designed to train each model being considered for the use case (i.e., each model selected for the library at stage 204). For example, stage 206 may include performing k-fold validation for each model (e.g., with k=10, where a model is trained and evaluated ten times across different 90/10 partitions of the dataset that was selected at stage 202). Within the machine learning pipeline, the dataset selected at stage 202 may first be transformed via standard scaling, such as by normalizing each feature to a mean of zero ($\mu=0$) and a standard deviation of one ($\sigma=1$). This allows the importance of each feature to be considered on an equal basis, without bias due to unequal magnitudes of raw values corresponding to different features.

After normalization, the hyperparameters of the model are tuned. For example, a Bayesian search technique may be used to tune the hyperparameters. This technique performs a Bayesian-guided search that is computationally more efficient than a grid search or a random search, yet yields similar levels of performance as a random search. Simpler algorithms, such as non-boosting and non-neural network algorithms, may use a relatively small number of iterations of Bayesian search (e.g., 10), while more complex algorithms such as gradient boosting, xgboost, and neural network algorithms may use a relatively large number of iterations of Bayesian search (e.g., 30), due to the higher-dimensional search space. The hyperparameters may be chosen through k-fold validation (e.g., with k=5). Each trained model, with its tuned hyperparameters, is then evaluated using the test dataset. Algorithm performance metrics such as the coefficient of determination ($R^2$) and root mean squared error (RMSE) may be captured for each model. RMSE may be calculated as:

$$RMSE \equiv \sqrt{\frac{1}{n}\sum_{i=1}^{n}(f_i - y_i)^2}, \quad \text{(Equation 2)}$$

where n represents the number of samples per cross-validation fold, y represents the true target output, and $f$ represents the predicted target output. Average RMSE for a model may be calculated as:

$$RMSE_{avg} = \frac{1}{k}\sum_{j=1}^{k} RMSE_j, \quad \text{(Equation 3)}$$

where k represents the number of cross-validation folds.

At stage 208, the best model for the use case is chosen, according to some criteria. For example, the "best" model may be the model, among all the models that are used to populate the model library at stage 204 and trained at stage 206, that has the lowest average RMSE across 10 cross-validation folds after 90/10 k-fold validation (per Equation 3, above). RMSE may be a better metric than $R^2$, because RMSE avoids the tendency to compare model performance between use cases with a singular, normalized metric. Furthermore, the $R^2$ metric can occasionally yield extremely negative values with some cross-validation sets, which can skew the model comparison dynamic when averaged. RMSE may be utilized over mean absolute error (MAE) in order to penalize larger errors between predictions and actual results.

Thereafter, at stage 210, a final production model for the use case is output. The final production model may be of the same type as the model that was selected at stage 208, but re-trained on the entire dataset selected at stage 202 to obtain better (e.g., optimal) hyperparameters. By training on the entire dataset, the final production model may generalize better, and exhibit a similar or higher level of average accuracy as compared to that obtained during cross-fold validation. The final production model is then stored as a trained model, and is ready to make predictions for new experiments.

In one embodiment, process 200 is performed by training server 104 of FIG. 2 (possibly with human input at various stages, such as defining use cases and/or populating the model library with candidate models). Process 200 may repeated for each use case, and for any suitable number of use cases (e.g., 5, 10, 100, etc.). As final production models for the different use cases are output at each iteration of stage 210, training server 104 may add those final production models to machine learning models 108. Thereafter, and prior to making predictions for various clones/cell lines of small-scale cell cultures (e.g., culture 110) in the manner discussed above with reference to FIG. 2, computing system 102 or training server 104 may select the appropriate final production model from models 108. The selection may be made based on user input indicating the use case (e.g., as discussed below with reference to FIG. 6A), and based on an algorithm or mapping (e.g., implemented by application 130) that matches the user-designated use case to the final production model. Alternatively, if no exact match exists, such an algorithm may match the user-designated use case to the final production model, of models 108, that was tailored to a use case that is most similar to the user-designated use case (e.g., as determined by calculating a vector distance between numerical parameters that define the use case, with categorical parameters such as modality being mapped to numerical values).

As noted above, it may be advantageous to reduce the number of features needed for a particular model. Therefore, when the "best" model from stage 208 is re-trained at stage 210, only those features that are most predictive of the desired output (e.g., titer, etc.) may be utilized. To identify the smaller feature set, the process 200 may implement recursive feature elimination (RFE), which allows for recursive reduction of explanatory features that are to be used in the final production model, discarding the least important features. The RFE algorithm trains on the data by utilizing a subset of features to yield optimal model performance with respect to a constraint on the number of features. Pairing RFE with sparsity-inducing models/estimators such as decision trees or elastic net can further reduce the number of explanatory features, in a trade-off that increases interpretability at the expense of model accuracy. Through RFE, an elbow plot can be used to determine the "sweet spot" or inflection point between interpretability and accuracy.

In addition to determining the accuracy of each model in the model library, it can be important to know the prediction interval (also known as the "confidence" interval). For example, a model with slightly lower accuracy may be preferred to a higher-accuracy model if the lower-accuracy model has a much tighter prediction interval. However, complex machine learning algorithms may only generate point predictions, without intervals. In some embodiments, therefore, a conformal prediction framework is utilized. Conformal prediction intervals allow for the assignment of error bounds for each new observation, and may be used as a wrapper for any machine learning estimator. This framework is applicable if the training and test data is assumed to come from the same distribution. If this exchangeability condition is satisfied, a subset of the training data can be utilized to build a nonconformity function from which the underlying sample distribution is measured.

In one embodiment, a "nonconformist" API is utilized with the inductive conformal prediction framework, which allows the model to be trained just once before prediction intervals are generated for all new observations, in parallel. The inductive conformal prediction framework requires a calibration set that is disjoint of the training set. While this helps build robust prediction intervals, removing samples from the training set to build the nonconformity function decreases the statistical power of the model. A normalization process (e.g., with a KNN-based approach) may be used to generate specific decision boundaries for each prediction.

While the prediction intervals generated by the conformal prediction framework contain the future observation in a proportion equal to $1-\alpha$ (with $\alpha$ being the significance level), the width of the generated intervals depends heavily on the underlying function. Naturally, narrower intervals instill greater confidence in the point prediction.

Figure 4A:
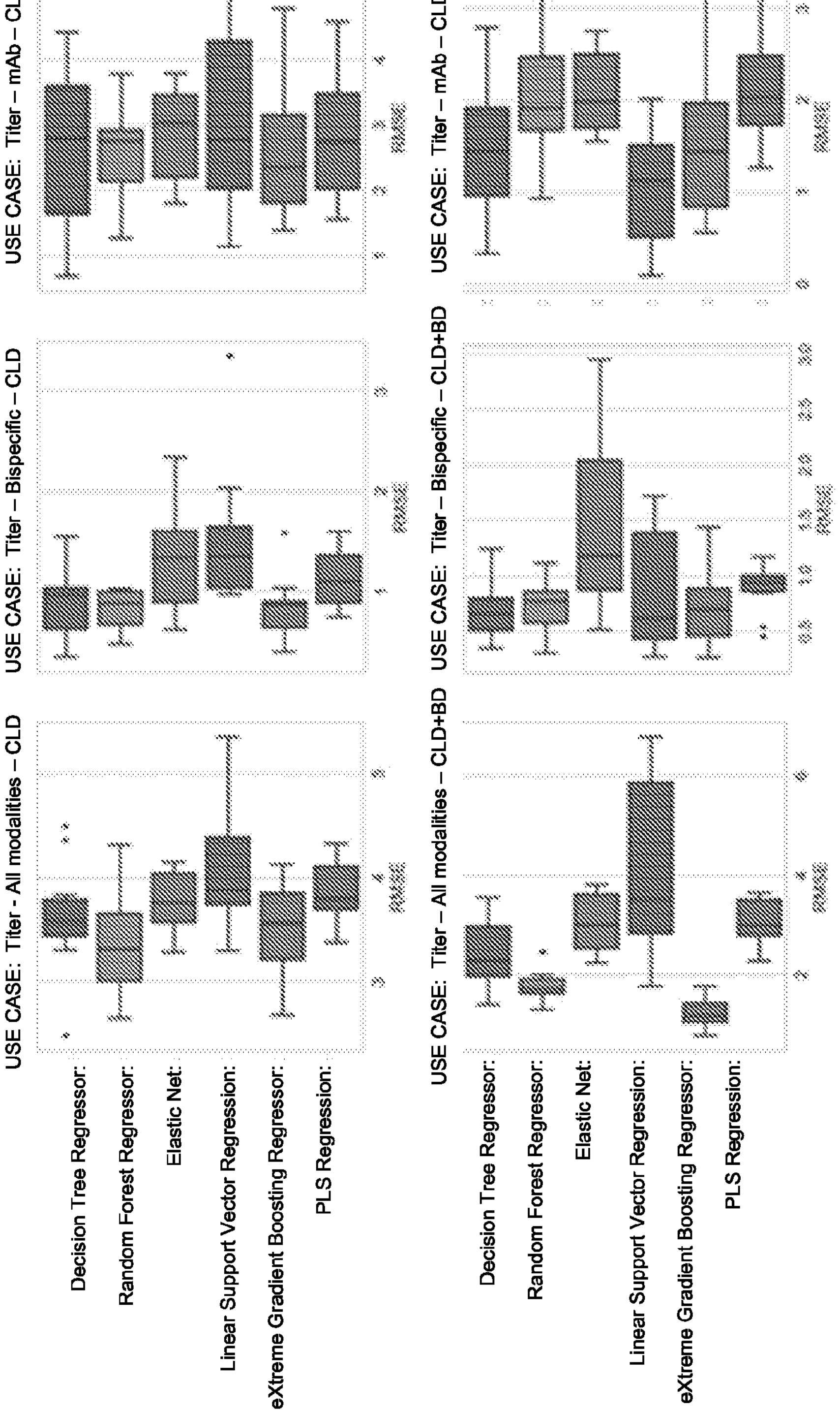
FIGS. 4A and 4B depict example performance for a variety of models in a variety of different use cases.
Figure 4B:
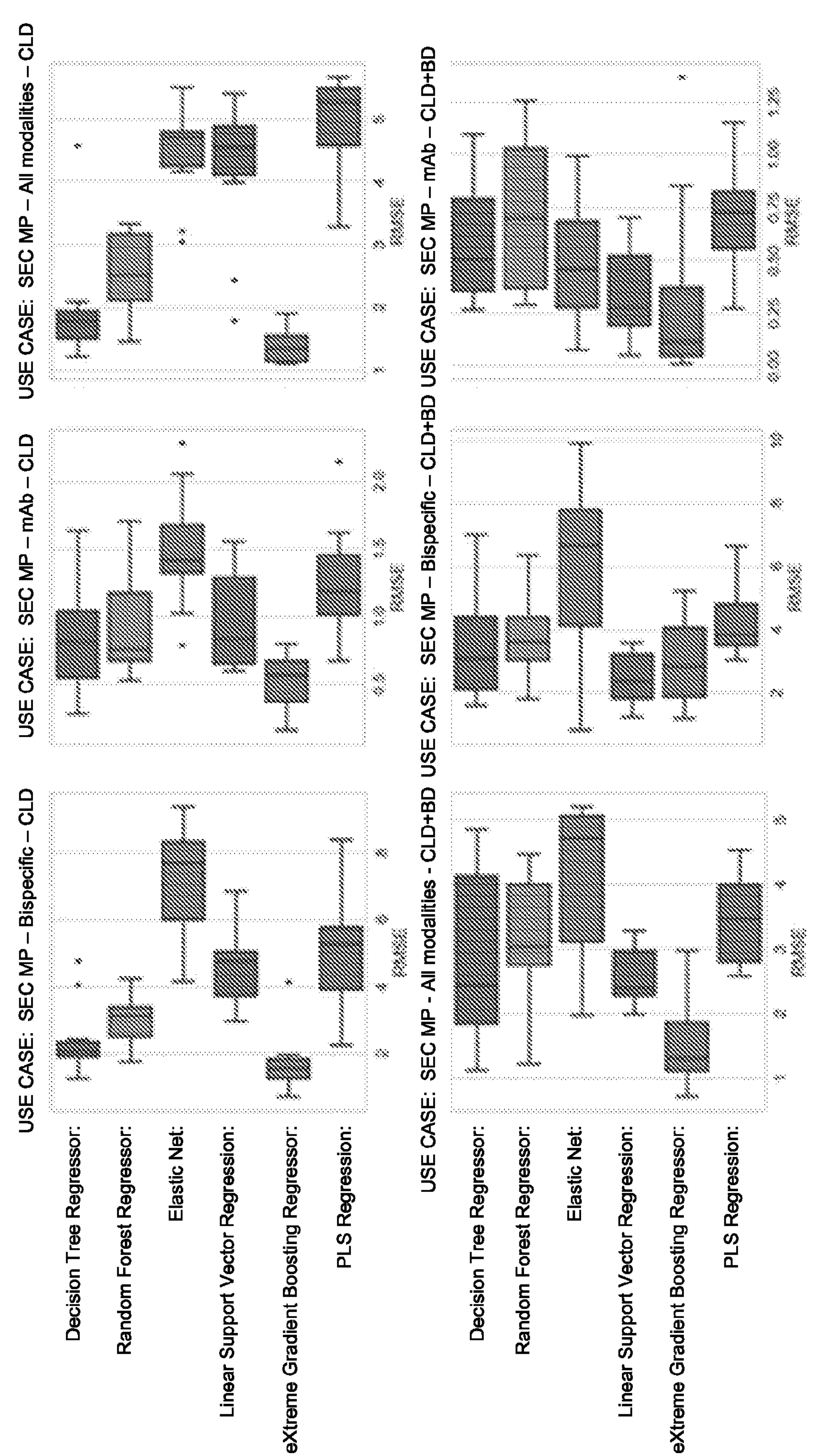

FIGS. 4A and 4B depict example model performance (here, RMSE across 10 folds of cross-validation) for a number of different use cases. In all use cases shown, the target variable (attribute value) is either large-scale (bioreactor) end-point titer or large-scale SEC analysis metrics. The bioreactor end-point titers may represent product concentration yield from harvested cell culture fluid (HCCF) on the last day of a perfusion bioreactor culture (e.g., Day 15). This is the weighted average combined titer from the culture supernatant and perfusion permeate. End-point titer is used to evaluate productivity. SEC analysis evaluates the chromatograph peak profiles of the product based on protein size. The three elution peaks are usually resolved into three classifications: low molecular weight (LMW), main peak (MP), and high molecular weight (HMW). A high-quality clone would ideally have high SEC MP, low SEC LMW, and low SEC HMW. MP represents usable product, LMW represents truncated clippings, and HMW represents clumped aggregates. SEC is one of several core analyses typically used to evaluate product quality.

In FIGS. 4A and 4B, "CLD" refers to cell line development to indicate that, for that use case, small-scale culture data is used to train the models, while "BD" refers to bioprocess development to indicate that, for that use case, large-scale culture data is also used to train the models. Thus, for example, the use case "Titer-All modalities-CLD" is one in which the target attribute value is bioreactor end-point titer, all modalities (e.g., mAb and bispecific or multispecific antibodies) are included, and only small-scale culture data is used to train the models. For each model in each plot, the thin horizontal line (with short vertical lines at each end) represents the total RMSE range over 10-fold cross-validation, the thick horizontal bar represents the +/−standard deviation range for the RMSE, and the vertical line within the thick horizontal bar represents the average RMSE across all 10 folds.

As seen in FIG. 4A, for instance, the random forest regressor model provides the lowest average RMSE for the use cases "Titer-All modalities-CLD" and "Titer-Bispecific-CLD," the xgboost model provides the lowest average RMSE for the use cases "Titer-mAb-CLD" and "Titer-All modalities-CLD+BD," the decision tree model provides the lowest average RMSE for the use case "Titer-Bispecific-CLD+BD," and the SVM (linear kernel) model provides the lowest average RMSE for the use case "Titer-mAb-CLD+BD." As seen in FIG. 4B, the xgboost model provides the lowest average RMSE for the use cases "SEC MP-All modalities-CLD," "SEC MP-Bispecific-CLD," "SEC MP-mAb-CLD," "SEC MP-All modalities-CLD_BD," and "SEC MP-mAb-CLD+BD," while the SVM (linear kernel) model provides the lowest average RMSE for the use case "SEC MP-Bispecific-CLD+BD."

While not shown in FIG. 4B, similar results can also be generated for SEC HMW and SEC LMW. For the SEC HMW target attribute value, the decision tree model provides the lowest average RMSE for the use cases "SEC HMW-All modalities-CLD," "SEC LMW-All modalities-CLD," "SEC LMW-Bispecific-CLD," and "SEC LMW-All modalities-CLD+BD," the xgboost model provides the lowest RMSE for the use cases "SEC HMW-Bispecific-CLD," "SEC HMW-mAb-CLD," " SEC HMW-Bispecific-CLD+BD," "SEC HMW-mAb-CLD+BD," and "SEC LMW-Bispecific-CLD+BD," the random forest model provides the lowest RMSE for the use case "SEC HMW-All modalities-CLD+BD," the elastic net provides the lowest RMSE for the use case "SEC LMW-mAb-CLD," and the SVM (linear kernel) model provides the lowest RMSE for the use case "SEC LMW-mAb-CLD+BD."

In some embodiments, application 130 of computing system 102 of FIG. 2 determines the use case (target attribute value, modality, and dataset type), for a given collection of candidate clones/cell lines, based on user inputs (e.g., entered via display 124), and requests the corresponding one of models 108 from training server 104. For example, models 108 may include all of the "lowest average RMSE" models indicated above, and server 104 or computing system 102 may store a database associating each of those models with the use case (or use cases) for which the model provided the lowest average RMSE. Server 104 or computing system 102 may then access that database to select the appropriate the best model for the determined use case. In an alternative embodiment, computing system 102 sends data indicative of the use case to training server 104, in response to which training server 104 selects the corresponding one of models 108 and sends that model to computing system 102 for storage as local machine learning model 136. In still other embodiments, as noted above, the selected model may be utilized remotely from computing system 102 (e.g., at server 104).

In some instances, users may wish to test two or more use cases in order to select a winning clone, or to select a set of clones to be scaled-up in bioreactors for further screening. In these instances, application 130 (or a remote server such as server 104) may select and run multiple models that are all used to make large-scale predictions for each clone/cell line. For example, a user may wish to consider both titer and SEC main peak at large-scale when selecting a winning clone. Thus, application 130 may select and/or run a first machine learning model for a use case corresponding to end-point titer (e.g., a random forest model), and a second machine learning model for a use case corresponding to SEC main peak (e.g., an xgboost model). As another example, a user may wish to consider titer, SEC main peak, SEC low molecular weight, and SEC high molecular weight at large-scale when selecting a winning clone, and application 130 may select and/or run a random forest model for titer, an xgboost model for SEC main peak, and a decision tree model for both SEC low molecular weight and SEC high molecular weight.

As noted above, interpretable models may be preferred in order to identify which inputs/features are most predictive of particular target attribute values. For example, tree-based learning methods may output metrics indicative of how important each feature is for purposes of reducing the mean square error of the model, when that feature is used as a node in the decision tree. Moreover, coefficient plots can represent the normalized, directional coefficients that weight each input/feature when predicting a target attribute value.

Figure 5A:
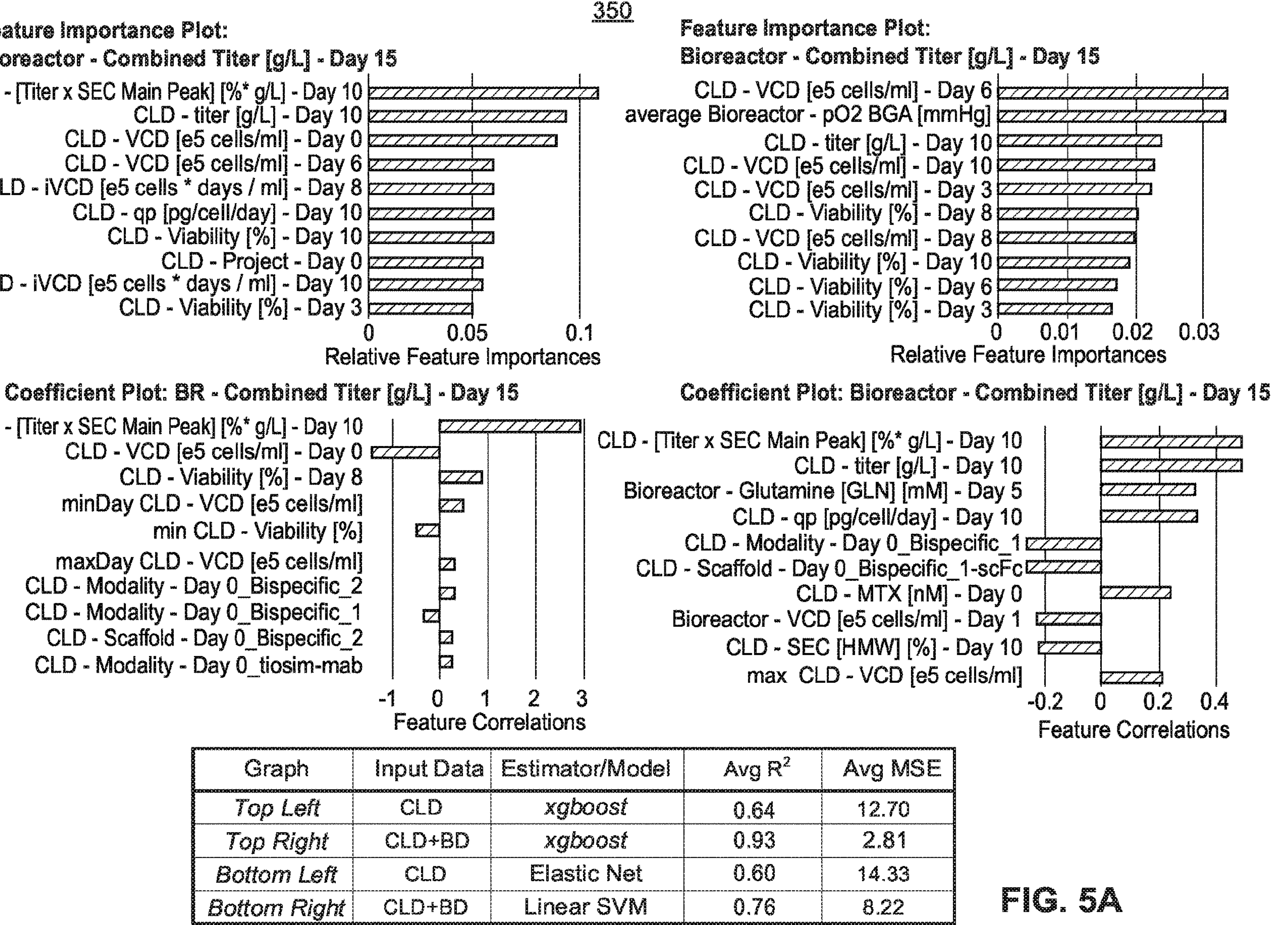
FIGS. 5A through 5D depict example feature importance metrics for a variety of different use cases and models.
Figure 5B:
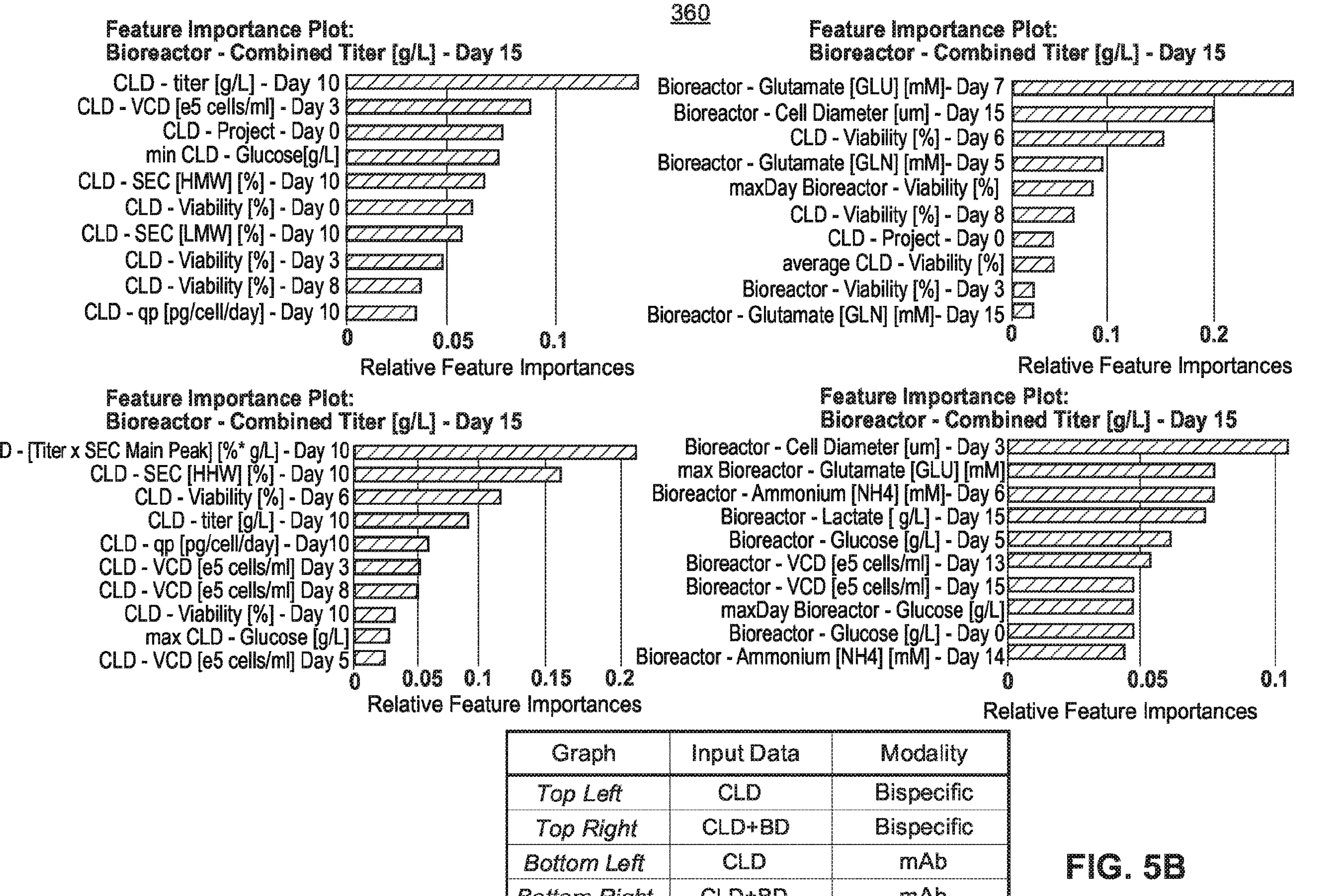

FIGS. 5A through 5D depict example feature importance metrics for a variety of different use cases and a variety of different models. FIG. 5A depicts feature importance plots and coefficient plots for models predicting large-scale (bioreactor) end-point titers, and FIG. 5B depicts feature importance plots for titer predictions that are filtered by modality. From these two plots, it can be seen that "CLD-Titer×SEC Main Peak-Day 10" is consistently a high-importance feature for models derived using exclusively CLD (cell line development) data. It can also be seen that VCD is a particularly important characteristic in predicting titer, more so than specific productivity (denoted as "qp," and having units of pg per cell per day). This indicates that, for purposes of generating high titers, there is greater importance in having better cell growth than having high specific productivity in a culture. The term "iVCD" in FIG. 5A refers to integrated VCD, which accounts for the total of the quantity (cell×days) in the reactor.

Figure 5C:
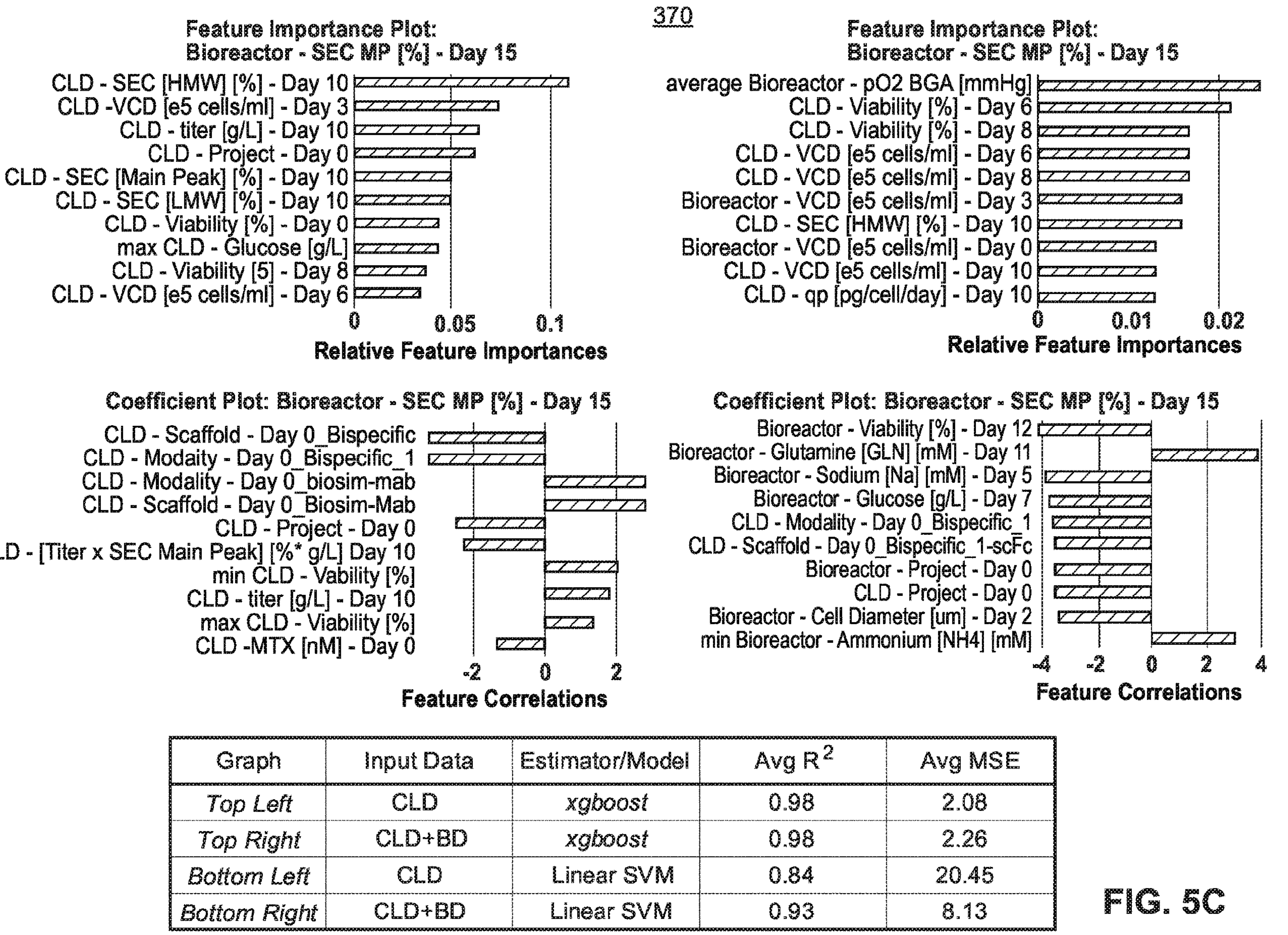
Figure 5D:
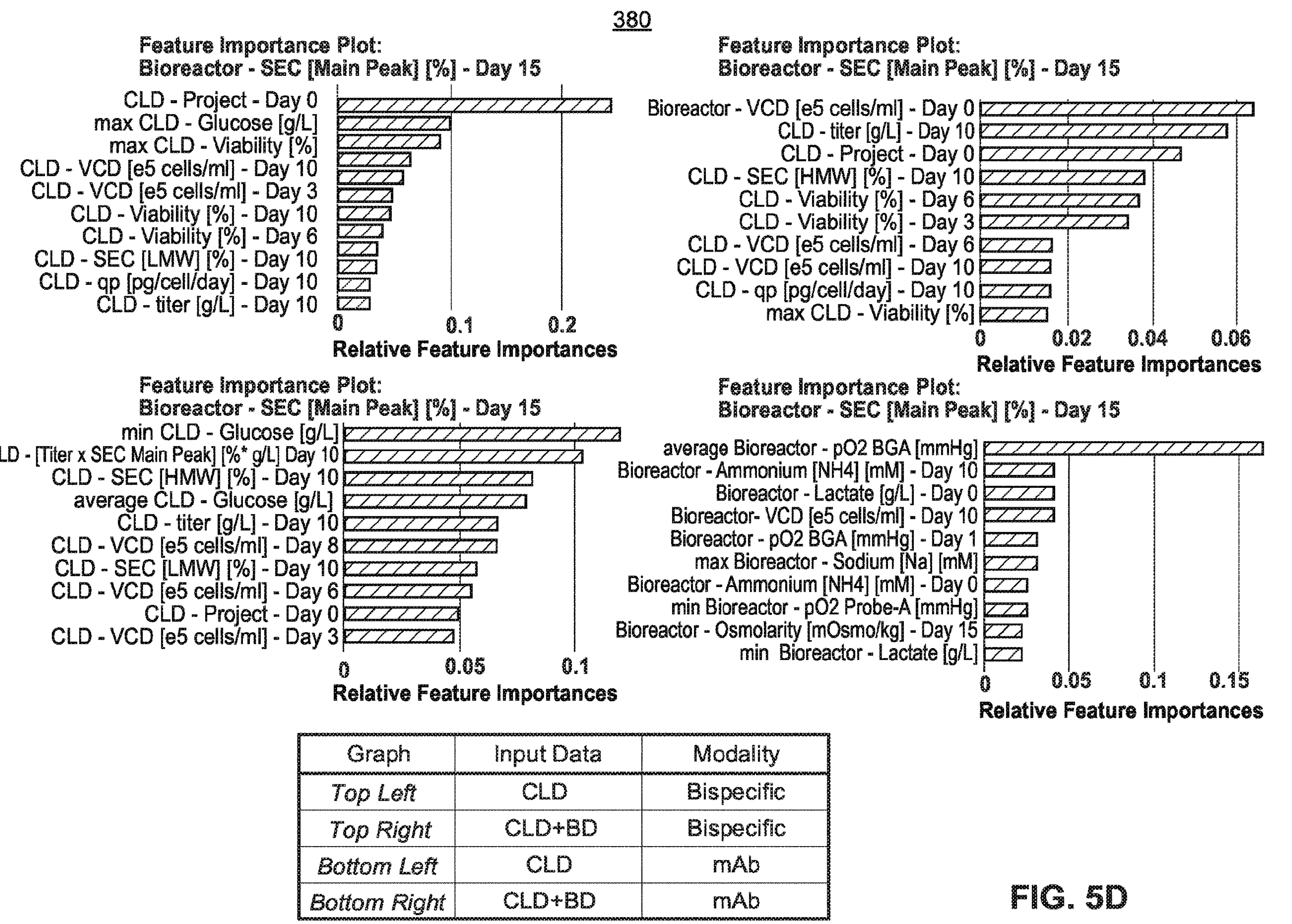

FIG. 5C depicts feature importance plots and coefficient plots for models predicting large-scale (bioreactor) end-point SEC main peak, and FIG. 5D depicts feature importance plots for SEC main peak predictions that are filtered by modality. From these plots, it can be seen that modality and modifications to the protein scaffold are key determinants of SEC main peak. For example, the CLD modality at Day 0 (converted to a numerical value) has a strong negative correlation with SEC main peak, indicating that molecules corresponding to a bispecific format generally have a lower expected SEC main peak. The term "Project" in FIG. 5D refers to an indicator of the specific project, and therefore the specific product.

In some embodiments, training server 104 of FIG. 2 uses the N most important features for a particular use case and model (N being a pre-determined positive integer, such as 10, or the number that results in greater than a threshold importance metric for every feature, etc.) to train any given model of machine learning models 108, and only those N features are collected by data collection unit 132 for processing by local model 136. In some embodiments, N is determined using recursive feature elimination (RFE), as noted above. Through RFE, training server 104 may perform multiple iterations of training to reduce the final number of inputs/features used to make a prediction. As noted above, the ideal number of features (i.e., the number of features used to train the various models 108 that are used in production) may be chosen by inspecting an elbow plot graphing number of features with model performance, for example, with the inflection point in each such graph representing the "sweet spot" between accuracy and interpretability.

Any suitable attributes may be used for the features discussed above (e.g., for initially training the various models, and possibly also for training the final production models, if the feature is of sufficient importance). A non-exhaustive list of possible attributes/features, for both the cell line development (CLD) and bioprocess development (BD) datasets, is provided in Table 1 below:

TABLE 1

| Feature | Dataset | Description | Type |
|---|---|---|---|
| Cell Line | CLD | | Cell Line characteristic |
| Modality | CLD | drug modality | Cell Line characteristic |
| Target | CLD | drug target | Cell Line characteristic |
| Scaffold | CLD | drug protein scaffold type | Cell Line characteristic |
| MTX [nM] | CLD | | Cell Line characteristic |
| Glucose [g/L] | CLD | | Cultue |
| Titer [g/L] | CLD | | Growth |
| VCD [e5 cells/mL] | CLD | | Growth |
| Viability [%] | CLD | | Growth |
| Project | CLD | program ID | Metadata |
| Clone | CLD | clone ID | Metadata |
| SEC [HMW] [%] | CLD | size-exclusion chromatography HMW peak area | Product quality attribute (PQA) |
| SEC [LMW] [%] | CLD | size-exclusion chromatography LMW peak area | PQA |
| SEC [Main Peak] [%] | CLD | size-exclusion chromatography main peak area | PQA |
| Sequence Component | CLD | drug sequence | Cell Line characteristic |
| Media | CLD | | Culture |
| Volume [mL] | CLD | | Culture |
| Vessel | CLD | | Culture |
| Lactate [g/L] | CLD | | Culture |
| Datasource | CLD | | Metadata |
| Duplicate ID | CLD | | Metadata |
| CEX [Acidic Peak] [%] | CLD | cation-exchange chromatography acid peak area | PQA |
| CEX [Basic Peak] [%] | CLD | cation-exchange chromatography basic peak area | PQA |
| CEX [Main Peak] [%] | CLD | cation-exchange chromatography main peak area | PQA |
| rCE [LC + HC] [%] | CLD | reduced capillary electrophoresis (combined light chain/heavy chain peak area) | PQA |
| rCE [LMW] [%] | CLD | reduced capillary electrophoresis (LMW peak area) | PQA |
| rCE [LC] [%] | CLD | reduced capillary electrophoresis (light chain peak area) | PQA |
| rCE [MMW] [%] | CLD | reduced capillary electrophoresis (medium molecular weight peak area) | PQA |
| rCE [HC] [%] | CLD | reduced capillary electrophoresis (heavy chain peak area) | PQA |
| rCE [Post HC] [%] | CLD | reduced capillary electrophoresis (post-heavy chain peak area) | PQA |
| rCE [HMW] [%] | CLD | reduced capillary electrophoresis (HMW peak area) | PQA |
| nrCE [Main Peak] [%] | CLD | non-reduced capillary electrophoresis (main peak area) | PQA |
| nrCE [Pre-Peaks] [%] | CLD | non-reduced capillary electrophoresis (pre-main peak area) | PQA |

TABLE 1-continued

| Feature | Dataset | Description | Type |
|---|---|---|---|
| nrCE [Post-Peaks] [%] | CLD | non-reduced capillary electrophoresis (post-main peak area) | PQA |
| Ammonium [NH4] [mM] | BD | | Culture |
| Sodium [Na] [mM] | BD | | Culture |
| Calcium [mM] | BD | | Culture |
| Glucose [g/L] | BD | | Culture |
| Glutamine [GLN] [mM] | BD | | Culture |
| Glutamine [GLN] [mM] | BD | | Culture |
| Potassium [K] [mM] | BD | | Culture |
| Lactate [g/L] | BD | | Culture |
| pO2 Probe-A [mmHg] | BD | | Culture |
| Osmolarity [mOsmo/kg] | BD | | Culture |
| pCO2 BGA [mmHg] | BD | partial pressure of CO2 from blood gas analyzer probe | Culture |
| pH BGA | BD | pH from blood gas analyzer probe | Culture |
| pH Probe-A | BD | | Culture |
| pO2 BGA [mmHg] | BD | partial pressure of oxygen from blood gas analyzer probe | Culture |
| Combined Titer [g/L] | BD | HCCF (culture supernatant + perfusion permeate) titer | Growth |
| PCV [%] | BD | packed cell volume in bioculture | Growth |
| PCV adj Titer [g/L] | BD | | Growth |
| VCD [e5 cells/ml] | BD | | Growth |
| Viability [%] | BD | | Growth |
| Yield [%] | BD | (Mass Cumulative Harvest)/(Mass Cumulative Harvested + Mass Bioreactor) | Growth |
| Cell Diameter [um] | BD | | Growth |
| Project | BD | program ID | Metadata |
| SEC [HMW] [%] | BD | size-exclusion chromatography HMW peak area | PQA |
| SEC [LMW] [%] | BD | size-exclusion chromatography LMW peak area | PQA |
| SEC [Main Peak] [%] | BD | size-exclusion chromatography main peak area | PQA |
| Media | BD | | Culture |
| Antifoam [g] | BD | | Culture |
| Cumulative Base Down [ml] | BD | | Culture |
| Cumulative Base Up [ml] | BD | | Culture |
| Cumulative Glucose [x] | BD | | Culture |
| Feed Volume [ml] | BD | | Culture |
| LDH [U/L] | BD | | Culture |
| Na2CO3 [ml] | BD | | Culture |
| Temperature [C.] | BD | | Culture |
| BR Volume [L] | BD | | Culture |
| Internal Bioreactor Volume [ml] | BD | | Culture |
| XMF Titer [g/L] | BD | permeate titer | Growth |
| BR Titer [g/L] | BD | bioreactor supermatant titer | Growth |
| BR Mass [g] | BD | | Growth |
| XMF Mass [G] | BD | | Growth |
| Permeate Line Titer [g/L] | BD | | Growth |
| Sieving [%] | BD | | Growth |
| HCCF Weight [kg] | BD | | Growth |
| Clone | BD | clone ID | Metadata |
| Datasource | BD | | Metadata |
| Pool or Clone | BD | | Metadata |
| RUN_NUMBER | BD | | Metadata |
| Reactor | BD | | Metadata |
| Run ID | BD | | Metadata |
| LEGEND_TEXT | BD | | Metadata |
| EXPMNT_OWNER | BD | | Metadata |
| CEX [Acidic] [%] | BD | cation-exchange chromatography acid peak area | PQA |
| CEX [Basic] [%] | BD | cation-exchange chromatography basic peak area | PQA |
| CEX [Main Peak] [%] | BD | cation-exchange chromatography main peak area | PQA |
| rCE [LC + HC] [%] | BD | reduced capillary electrophoresis (combined light chain/heavy chain peak area) | PQA |
| rCE [LMW] [%] | BD | reduced capillary electrophoresis (LMW peak area) | PQA |
| rCE [LC] [%] | BD | reduced capillary electrophoresis (light chain peak area) | PQA |
| rCE [MMW] [%] | BD | reduced capillary electrophoresis (medium molecular weight peak area) | PQA |
| rCE [HC] [%] | BD | reduced capillary electrophoresis (heavy chain peak area) | PQA |
| rCE [POST HC] [%] | BD | reduced capillary electrophoresis (post-heavy chain peak area) | PQA |

TABLE 1-continued

| Feature | Dataset | Description | Type |
|---|---|---|---|
| rCE [HMW] [%] | BD | reduced capillary electrophoresis (HMW peak area) | PQA |
| nrCE [Main Peak] [%] | BD | non-reduced capillary electrophoresis (main peak area) | PQA |
| nrCE [Pre-Peaks] [%] | BD | non-reduced capillary electrophoresis (pre-main peak area) | PQA |
| HILIC [Afucosylated] [%] | BD | HILIC afucosylated glycan peak area | PQA |
| HILIC [High Manose] [%] | BD | HILIC high manose glycan peak area | PQA |
| HILIC [Sialylation] [%] | BD | HILIC sialyiation glycan peak area | PQA |
| BR-only SEC [Main Peak] [%] | BD | SEC main peak area of product from bioreactor only | PQA |
| UPLC [Monomer] [%] | BD | | PQA |

Figure 6A:
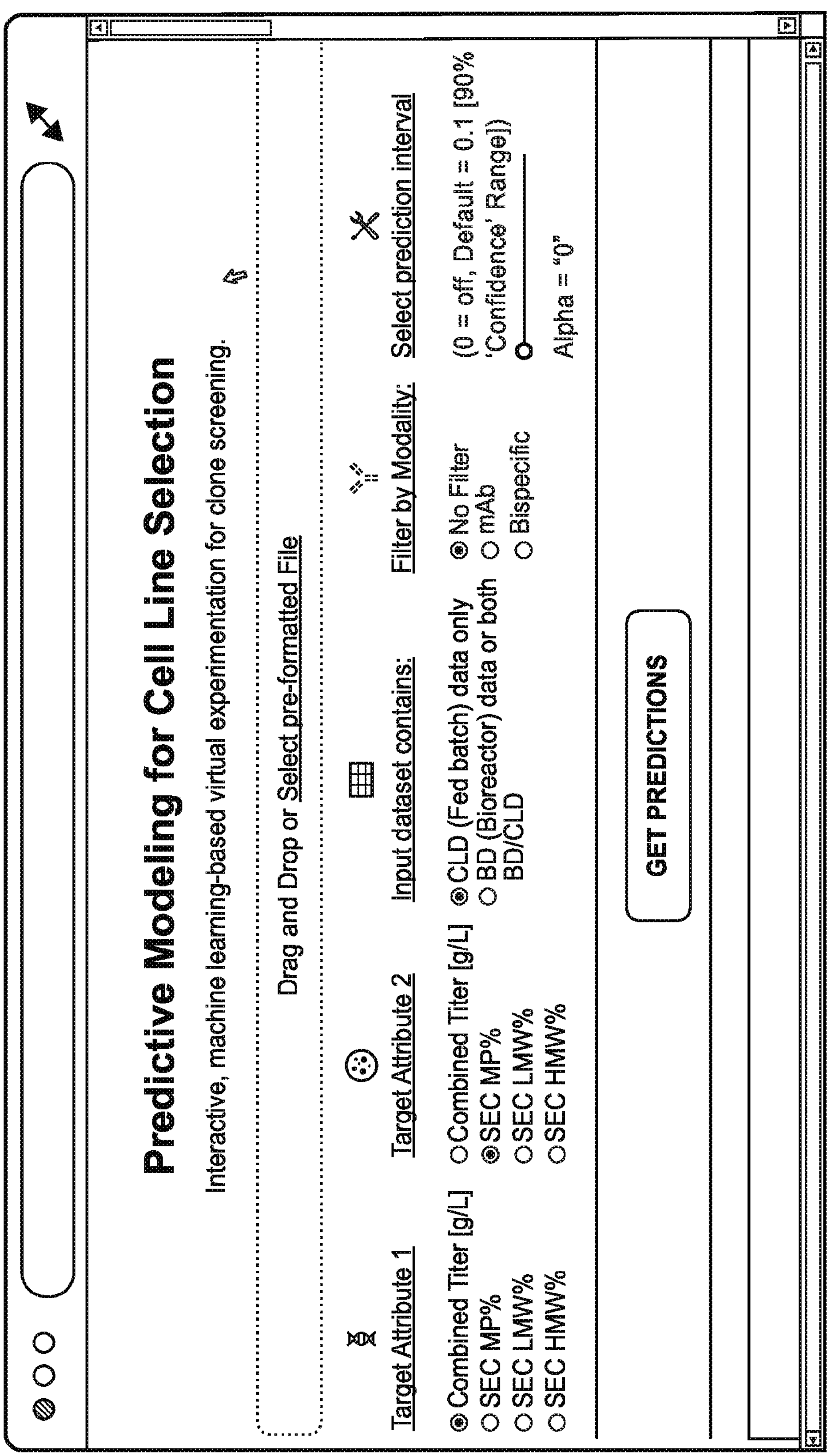
FIGS. 6A and 6B depict screenshots provided by an example user interface for setting use case parameters and analyzing prediction outputs, respectively.

As noted above, the machine learning model or models (e.g., of models 108) that are selected (e.g., by application 130 or server 104) to make large-scale culture predictions may depend upon the use case, or series of use cases, that is/are entered by a user via a graphical user interface. FIG. 6A depicts an example screenshot 400 of such a user interface, which application 130 may cause to be presented on display 124, for example. As seen in the example embodiment of FIG. 6A, the user interface may enable a user to (1) enter two target attributes (i.e., the large-scale, bioreactor attributes to be predicted by corresponding machine learning models), (2) indicate whether the inputs/features should include only cell line development data, or both cell line development and bioprocess development (bioreactor) data, (3) indicate the modality or modalities under consideration, and (4) indicate a desired prediction/confidence interval. Based on the user inputs, application 130 or server 104 may select the appropriate models, from models 108, for making the predictions, i.e., the final production models resulting from stage 210 of process 200 for each of the user-indicated use cases. For the example screenshot 400, it can be seen that a single set of user inputs may correspond to two use cases (i.e., one for each of the two target attributes, with each of those use cases including the same user-selected dataset and modality). The selected models may be downloaded as local models (e.g., each similar to model 136) or may remain at server 104 for use in a cloud service. User activation of the "Get Predictions!" control is detected by application 130 (or server 104), in response to which application 130 (or server 104) causes the models to act upon the respective feature sets and predict the respective large-scale attribute values. It is understood that, in other embodiments, the user interface may provide different user controls than those shown in FIG. 6A.

Figure 6B:
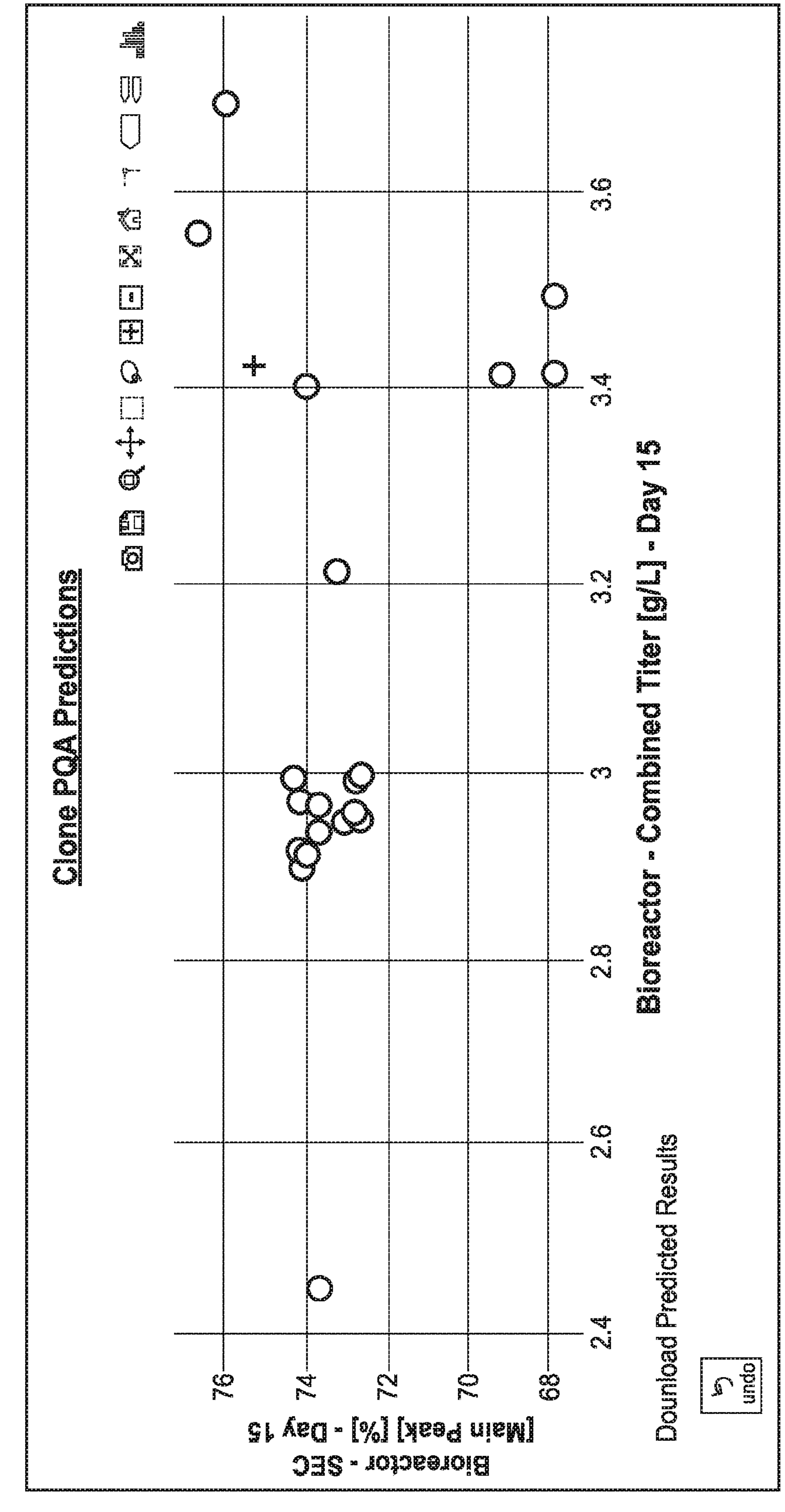

The predictions made by the selected/applied models may be presented to a user in any suitable manner. One example of such a presentation is depicted in screenshot 410 of FIG. 6B, which corresponds to an embodiment in which the predictions for all clones/cell lines can be depicted simultaneously. In FIG. 6B, each clone/cell line is plotted as a dark circle on a two-dimensional graph. For the results shown in the example scenario of FIG. 6B, a user desiring a clone with a high SEC main peak and a high titer would likely select (or, alternatively, application 130 would automatically select) one or both of the two clones in the upper right corner of the graph as the top clone(s). In some embodiments, application 130 also enables a user to toggle a display of the prediction interval for each prediction. Moreover, in some embodiments, application 130 enables a user to view feature importance and/or coefficient plots that are associated with the various models/predictions (e.g., plots similar to those shown in FIGS. 5A through 5D).

Figure 7:
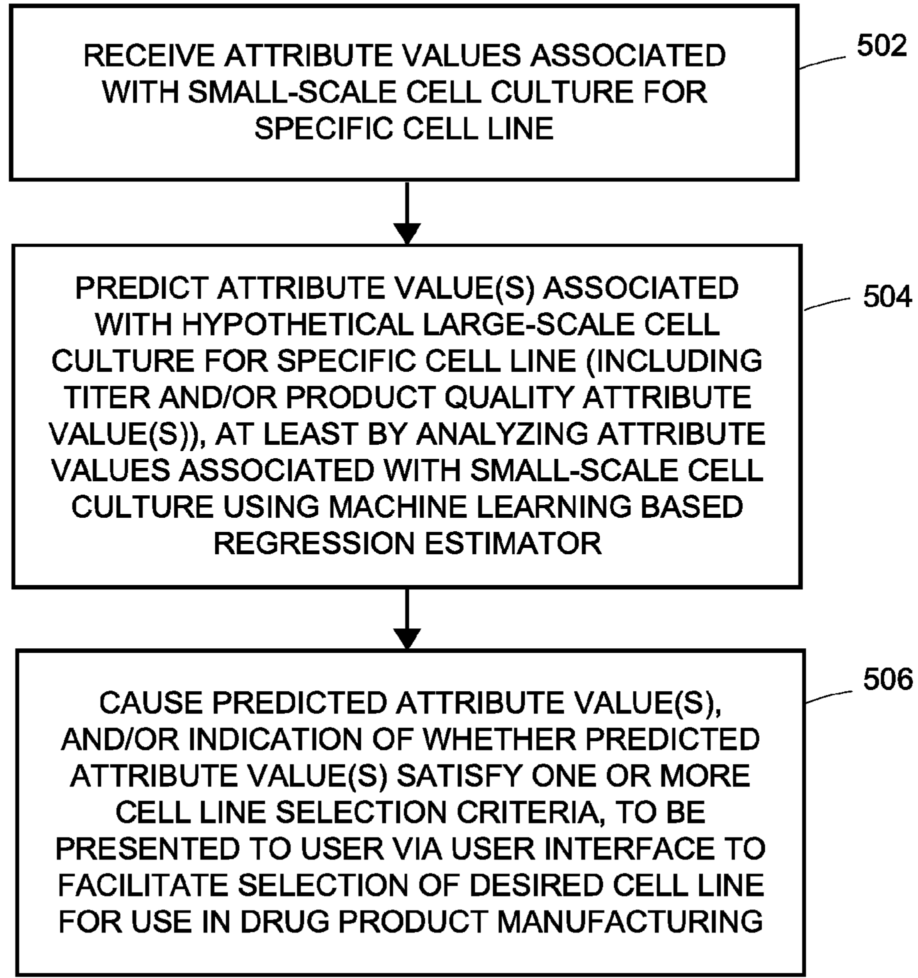
FIG. 7 is a flow diagram of an example method for facilitating selection of a master cell line from among candidate cell lines that produce recombinant proteins.

FIG. 7 is a flow diagram of an example method 500 for facilitating selection of a master cell line from among candidate cell lines that produce recombinant proteins. The method 500 may be implemented by processing unit 120 of computing system 102 when executing the software instructions of application 130 stored in memory unit 128, or by one or more processors of server 104 (e.g., in a cloud service implementation), for example.

At block 502, attribute values associated with a small-scale cell culture for a specific cell line are received. At least some of the received attribute values are measurements of the small-scale cell culture (e.g., end-point titer, SEC MP, SEC LMW, SEC HMW, VCD, viability, one or more media characteristics such as glucose or other metabolite concentrations, and/or any other CLD measurement value(s) shown above in Table 1). In some embodiments, the attribute values may be received from an opto-electronic instrument as described herein. In some embodiments and/or scenarios, other data is also received at block 502, such as user-entered data (e.g., an identifier of the specific cell line, a modality of a drug to be produced using the specific cell line, an indication of the drug product to be produced using the specific cell line, and/or a protein scaffold type associated with the drug to be produced using the specific cell line). Additionally, in some embodiments, one or more attribute values associated with a large-scale cell culture may be received (e.g., in an embodiment where the small-scale culture is scaled-up to make large-scale measurements at Day 0, in order to better predict large-scale performance at Day 15 without necessarily running the full-term large-scale culture).

In some embodiments, the small-scale culture attribute values received at block 502 include measurements obtained at different days of the small-scale culture. For example, a first attribute value may be a titer value at Day 10 of the small-scale culture (e.g., the end-point titer for a 10-day culture), while a second attribute value may be a VCD value at Day 0 of the small-scale culture. As a further example, a third attribute value may be a VCD value at Day 6 of the small-scale culture, and so on. In other exemplary embodiments, combinations of small-scale measurements may be the same as or similar to those shown with the label "CLD" in any of the plots of FIGS. 5A through 5D.

At block 504, one or more attribute values, associated with a hypothetical large-scale cell culture for the specific cell line, is/are predicted, at least by analyzing the attribute values (and possibly user-entered data) received at block 502 using a machine learning based regression estimator (e.g., a decision tree regression estimator, a random forest regression estimator, an xgboost regression estimator, a linear SVM regression estimator, etc.). The predicted attribute value(s) may include a titer (e.g., end-point titer) and/or one or more product quality attribute values (e.g., chromatography measurements such as SEC main peak, SEC LMW, and/or SEC HMW), for example.

At block 506, the predicted attribute value(s), and/or an indication of whether the predicted attribute value(s) satisfy one or more cell line selection criteria (e.g., exceed, or are below, some threshold value), are caused to be presented to a user via a user interface (e.g., the user interface corresponding to screenshot 410 of FIG. 6B), to facilitate the selection of a desired cell line for use in drug product manufacturing. For example, a user may proceed directly from such a display to select a "winning" cell line, or may use the displayed information to identify which cell lines should be scaled-up in real-world bioreactors for validation and/or further clone screening (with selection of the winning clone occurring at a subsequent stage).

In some embodiments, method 500 includes one or more additional blocks not shown in FIG. 7. For example, method 500 may include two additional blocks that both occur prior to block 502: a first additional block in which data indicative of a use case is received from a user via a user interface (e.g., the user interface corresponding to screenshot 400 of FIG. 6A), and a second additional block in which the machine learning based regression estimator is selected, based on the data indicative of the use case, from among a plurality of estimators (e.g., from among models 108), with each of those estimators having been designed/optimized for a different use case. For example, the user-entered data may be indicative of at least one of the one or more attribute value(s) associated with the hypothetical large-scale cell culture, indicative of a modality of a drug to be produced, and possibly also indicative of other parameters (e.g., a parameter denoting the scope of the dataset, such as the CLD and BD datasets discussed above).

In a more specific embodiment and scenario, the user-entered data indicative of the use case may include data indicative of at least a titer associated with the hypothetical large-scale cell culture, and block 504 may include analyzing the plurality of attribute values using a decision tree regression estimator, a random forest regression estimator, an xgboost regression estimator, or a linear SVM regression estimator (e.g., in accordance with the results discussed above in connection with FIG. 4A). As another specific embodiment and scenario, the user-entered data indicative of the use case may include data indicative of at least a chromatography measurement (e.g., SEC main peak) associated with the hypothetical large-scale cell culture, and block 504 may include analyzing the plurality of attribute values using an xgboost regression estimator (e.g., in accordance with the results discussed above in connection with FIG. 4B).

In embodiments where the machine learning based regression estimator is selected from among a plurality of estimators, method 500 may include an additional block in which, for each of the estimators, a set of features most predictive of an output of the estimator is determined. In such an embodiment, block 502 may include receiving only attribute values that are included within that set of most-predictive features.

FIG. 8 is a simplified block diagram of an example system 800 that may implement the techniques of the second aspect described herein. System 800 includes a computing system 802 communicatively coupled to a training server 804 via a network 806. Generally, computing system 802 is configured to determine/predict a ranking of candidate cell lines according to each of one or more product quality attributes (e.g., specific productivity, titer, and/or cell growth) in hypothetical small-scale screening cultures (e.g., fedbatch cultures), based on measurements by a clone (or cell line) generation and analysis system 850 and measurements at one or more cell pools 810, using one or more machine learning (ML) models 808 trained by a training server 804.

Network 806 may be similar to network 106 of FIG. 2, and/or training server 804 may be similar to training server 104. In the depicted embodiment, machine learning model(s) 808 is/are trained by training server 804, and then transferred to computing system 802 via network 806 as needed. In other embodiments, however, one, some or all of ML model(s) 808 may be trained on computing system 802, and then uploaded to server 804. In other embodiments, computing system 802 trains and maintains/stores the ML model(s) 808, in which case system 800 may omit both network 806 and training server 804. In still other embodiments, training server 804 provides access to the model(s) 808 as a web service (e.g., computing system 802 provides input data that server 804 uses to make a prediction with one or more of model(s) 808, and server 804 returns the results to computing system 802).

Each of cell pool(s) 810 may be a pool of transfected cells (e.g., Chinese hamster ovary (CHO) cells) within a single container, such as a well or vial, for example. The cell pool(s) 810 may be any suitable pool(s) of cells, scaled up through successive cell passages in selective growth media, that produce recombinant proteins, and may be of any modality. The cells may be cells that produce a recombinant protein such as a monoclonal antibody (mAb), or cells that produce a recombinant protein such as a bispecific or other multispecific antibody, for example. Generally, however, the cells of each of pool(s) 810 are not all clonally derived.

One or more analytical instruments 812 are configured, collectively, to obtain physical measurements of the cell pool(s) 810 that may be used by computing system 802 to make predictions, as discussed further herein. Analytical instrument(s) 812 may obtain the measurements directly, and/or may obtain or facilitate indirect or "soft" sensor measurements. As noted above, the term "measurement" as used herein may refer to a value that is directly measured/sensed (e.g., by one of instrument(s) 812), a value that is computed based on one or more direct measurements, or a value that a device other than the measuring device (e.g., computing system 802) computes based on one or more direct measurements. Analytical instrument(s) 812 may be similar to analytical instruments 112 of FIG. 2, for example, for example a chromatograph as described herein or an optical sensor. Analytical instruments 812 may include one or more devices specifically configured to measure cell pool viable cell density (VCD), cell pool viability (VIA), time integral viable cell density (IVCD), and cell pool specific productivity, for example.

The clone generation and analysis system 850 may be any suitable (preferably high-throughput) subcloning system. In some embodiments, the clone generation and analysis system 850 is a Berkeley Lights Beacon system. As seen in FIG. 8, the system 850 includes an analytical unit 852 and a cell line generation and growth unit 854. Cell line generation and growth unit 854 may be a culturing chip containing a plurality of physically isolated pens perfused by microfluidic channels. The unit 854 may be an OptoSelect™ Berkeley Lights chip, for example. Each of the pens may receive a transfected cell from a cell pool with the aid of projected light patterns that activate photoconductors, which gently repel cells to manipulate those cells (e.g., as provided by Berkeley Lights' OptoElectro™ positioning technology), and contain the cell (and other generated cells of the cell line) throughout a cell line generation and analysis process.

Analytical unit 852 of the cell line generation and analysis system 850 is configured to measure physical characteristics of cells in clone generation and growth unit 854. The analytical unit 852 may include one or more sensors or instruments to obtain the measurements directly, and/or may obtain or facilitate indirect or "soft" sensor measurements. Instruments of the analytical unit 852 may include instruments that are fully automated, and/or instruments that require human assistance. As just one example, instruments of the analytical unit 852 (e.g., sensors or other instruments integrated within, or interfacing with, unit 854) may include one or more imaging devices (e.g., a camera and/or microscope) and associated software configured to directly or indirectly measure cell count or cell growth, one or more devices configured to directly or indirectly measure cell productivity by performing secretion assays (e.g., diffusion-based fluorescence assays that bind to antibodies produced by the cells on the chip, such as a secretion assay using a Spotlight Hulg2 Assay (or Spotlight Assay)), and so on.

Computing system 802 may be a general-purpose computer similar to the computing system 102, for example. As seen in FIG. 8, computing system 802 includes a processing unit 820, a network interface 822, a display 824, a user input device 826, and a memory unit 828. Processing unit 820, network interface 822, display 824, and user input device 826 may be similar to processing unit 120, network interface 122, display 124, and user input device 126, respectively, of FIG. 2, for example.

Memory unit 828 may be similar to memory unit 128 of FIG. 2. Collectively, memory unit 828 may store one or more software applications, the data received/used by those applications, and the data output/generated by those applications. These applications include a small-scale prediction application 830 that, when executed by processing unit 820, ranks candidate cell lines according to each of one or more product quality attributes (e.g., specific productivity, titer, and/or cell growth) in hypothetical small-scale screening cultures (e.g., stage 12 of FIG. 1), based on the measurements obtained by analytical instruments 812 and analytical unit 852, and possibly also based on other information (e.g., modality, cell pool identifier, etc.). While various units of application 830 are discussed below, it is understood that those units may be distributed among different software applications, and/or that the functionality of any one such unit may be divided among two or more software applications.

In some embodiments, computing system 802, training server 804, and network 806 are computing system 102, training server 104, and network 106, respectively, and the memory unit (128 and 828) stores both the small-scale prediction application 830 and the large-scale prediction application 130. That is, the system (10 and 800) may be capable of predicting both small-scale and large-scale performance, with FIG. 8 representing a different use case than that shown in FIG. 2.

A data collection unit 832 of application 830 generally collects values of various attributes associated with cell pool(s) 810 and cell line generation and growth unit 854. For example, data collection unit 832 may receive measurements directly from analytical instrument(s) 812 and/or analytical unit 852. Additionally or alternatively, data collection unit 832 may receive information stored in a measurement database (not shown in FIG. 8) and/or information entered by a user (e.g., via user input device 826). For example, data collection unit 832 may receive a modality, target drug product, drug protein scaffold type, and/or any other suitable information entered by a user and/or stored in a database.

A prediction unit 834 of application 830 generally operates on the attribute values collected by data collection unit 832 to predict product quality attribute values for hypothetical small-scale screening cultures of the different candidate cell lines, using a local machine learning model 836, and uses the predicted values to rank the cell lines. In the depicted embodiment, machine learning model 836 is a local copy of one of the model(s) 808 trained by training server 804, and may be stored in a RAM of memory unit 828, for example. As noted above, however, server 804 may utilize/run model(s) 808 in other embodiments, in which case no local copy need be present in memory unit 828.

A visualization unit 838 of application 830 generates a user interface that presents rankings (determined by prediction unit 834) to a user. Visualization unit 838 may also enable a user to interact with the presented data from the prediction unit 834 via user input device 826 and display 824, and/or to enter parameters for a particular prediction or ranking (e.g., selecting a product quality attribute according to which predicted performance is to be ranked, etc.).

Operation of system 800, according to one embodiment, will now be described in further detail, for the specific scenario in which application 830 is used to determine one or more cell line rankings according to one or more small-scale culture product quality attributes. By ranking cell lines in this manner, the methodology for selecting top cell lines may be standardized, and a better selection of cell lines may be identified for small-scale screening, or the small-scale screening stage may be skipped entirely (e.g., by passing straight from stage 11 to stage 14 of process 10, based on the rankings for the various cell lines).

Initially, training server 804 trains machine learning model(s) 808 using data stored in a training database 840. Machine learning model(s) 808 may include a number of different types of machine learning based regression estimators (e.g., a random forest regressor model, an eXtreme gradient boosting (xgboost) regressor model, a linear regression model, a ridge regression model, a lasso regression model, a principal component analysis (PCA) with linear regression model, a partial least squares (PLS) regression, etc.), and possibly also one or more models not based on regression (e.g., a neural network). Moreover, model(s) 808 may include more than one model of any given type (e.g., two or more models of the same type that are trained on different historical datasets and/or using different feature sets), in some embodiments. Furthermore, different models of models 808 may be trained to predict values of different product quality attributes (e.g., titer, growth, or specific productivity, etc.), in order to facilitate the ranking of cell lines (by prediction unit 834) according to those different product quality attributes. Moreover, the machine learning model(s) 808 may be used to identify which features (e.g., which attribute values from the cell pool stage and/or clone generation and analysis stage) are most predictive of relative performance for candidate cell lines, for each of one or more small-scale culture product quality attributes. Model(s) 808 may also be trained or re-trained using a feature set that only includes the most predictive features.

Training database 840 may include a single database stored in a single memory (e.g., HDD, SSD, etc.), multiple databases stored in a single memory, a single database stored in multiple memories, or multiple databases stored in multiple memories. For each different model within machine learning model(s) 808, training database 840 may store a corresponding set of training data (e.g., input/feature data, and corresponding labels), with possible overlap between the training data sets. To train a model that predicts titer value for hypothetical small-scale cultures, for example, training database 840 may include numerous training data sets each comprising historical measurements of cell pool titer, cell productivity scores, and/or other measurements made by one or more instruments (e.g., by analytical instrument(s) 812, by instruments of analytical unit 852, and/or other instruments/sensors), along with a label for each training data set. In this example, the label for each training data set indicates the titer that was actually measured for that cell line at a small-scale culture stage.

In some embodiments, training server 804 uses additional labeled data sets in training database 840 in order to validate the trained machine learning model(s) 808 (e.g., to confirm that a given one of machine learning model(s) 808 provides at least some minimum acceptable accuracy). In some embodiments, training server 804 also updates/refines one or more of machine learning model(s) 808 on an ongoing basis. For example, after machine learning model(s) 808 is/are initially trained to provide a sufficient level of accuracy, additional measurements at cell pool and subcloning stages (features) and small-scale culture stages (labels) may be used to improve prediction accuracy.

After model(s) 808 is/are sufficiently trained, application 830 may retrieve, from training server 804 via network 806 and network interface 822, a specific one of machine learning models 808 that corresponds to a specific product quality attribute for which a ranking of candidate cell lines is desired. By way of example, a product quality attribute may comprise cell growth and the machine learning model may comprise PLS; or a product quality attribute may comprise specific productivity and the machine learning model may comprise PCA; or a product quality attribute may comprise titer and the machine learning model may comprise a ridge regression model. The product quality attribute may be one that was indicated by a user via a user interface (e.g., via user input device 826 and display 824, and a user interface generated by visualization unit 838), or based on any other suitable input. Upon retrieving the model, computing system 802 stores a local copy as local machine learning model 836. In other embodiments, as noted above, no model is retrieved, and input/feature data is instead sent to training server 804 (or another server) as needed to use the appropriate model of model(s) 808.

In accordance with the feature set used by model 836, data collection unit 832 collects the necessary data. For example, data collection unit 832 may communicate with analytical instrument(s) 812 and analytical unit 852 to collect measurements of titer, pool VCD, pool VIA, cell counts, cell productivity scores, and/or other specific attributes of cell pool(s) 810 and/or cell line generation and growth unit 852. In one such embodiment, data collection unit 832 sends commands to one or more of analytical instrument(s) 812 and one or more instruments of the analytical unit 852 to cause the one or more instruments to automatically collect the desired measurements. In another embodiment, data collection unit 832 collects the measurements of cell pool(s) 810 and cell line generation and growth unit 852 by communicating with a different computing system (not shown in FIG. 8) that is coupled to (and possibly controls) analytical instrument(s) 812 and/or analytical unit 852. As noted above, data collection unit 832 may also receive information entered by a user (e.g., modality). In some embodiments, application 830 uses some user-entered information collected by data collection unit 832 to select an appropriate one of models 808, and uses other user-entered information collected by data collection unit 832 as one or more features/inputs to the selected model (or to calculated the feature(s)/input(s)).

After data collection unit 832 has collected the attribute values that are associated with cell pool(s) 810 and cell line generation and growth unit 854 and are used as inputs/features by local machine learning model 836, prediction unit 834 causes model 836 to operate on those inputs/features to predict a value of the product quality attribute of interest (e.g., titer, growth, or specific productivity) for each of the candidate cell lines. Prediction unit 834 then compares the predicted values to each other to order/rank the cell lines from best to worst, or from worst to best. Importantly, it has been found that while machine learning models may generally have low accuracy with respect to predicting important product quality attributes in small-scale cultures, certain models (e.g., as discussed herein) nonetheless do well in terms of predicting relative values, such that the rankings of candidate cell lines are largely accurate even if the predicted values used to form those rankings have low accuracy.

Visualization unit 838 may cause a user interface, presented on display 824, to show the determined ranking of cell lines. The above process may be repeated by retrieving different ones of model(s) 808 that were trained specifically for one or more other product quality attributes of interest, collecting (by data collection unit 832) the inputs/features used by those models, using (e.g., by prediction unit 834) the models to predict the other product quality attributes for each of the candidate cell lines, and ranking (e.g., by prediction unit 834) the candidate cell lines according to those other product quality attributes. Visualization unit 838 may then cause the user interface to present all of the cell line rankings (e.g., one for titer, one for cell growth, and one for specific productivity) to enable a user to make a more informed choice as to which cell line or lines to advance to (or possibly, bypass) the small-scale culture stage.

Prediction unit 834 may store the predictions made by model 836 for each set of candidate cell lines, and/or the corresponding rankings, in memory unit 828 or another suitable memory/location. After predictions and/or rankings have been made and stored for all candidate cell lines under consideration, and for all product quality attributes of interest, a "winning" portion of candidate cell lines may be selected for advancement to a small-scale culture stage (e.g., to stage 14 of FIG. 1). The selection of winning cell line(s) may be fully automated according to some criteria specific to product quality attribute (e.g., by assigning specific weights to titer, cell growth, and specific productivity rankings and then comparing the resulting scores), or may involve human interaction (e.g., by displaying the predicted rankings to a user via display 824). The winning cell line(s) may then be advanced to a small-scale cell culture stage (e.g., to stage 12 of FIG. 1) or, in some embodiments, may be advanced to a future stage (e.g., to stage 14 of FIG. 1) by bypassing the small-scale cell culture stage.

Figure 9:
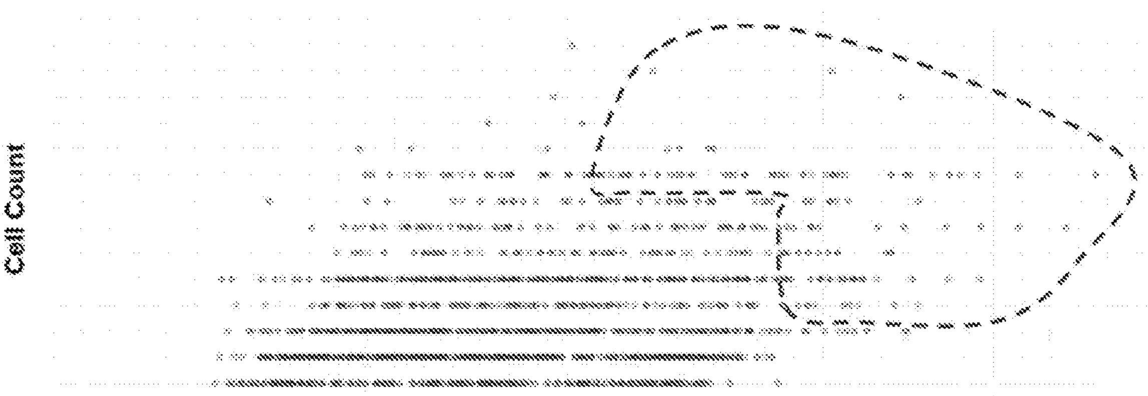
FIG. 9 is an example graphical output indicating a relation between cell counts and cell productivity scores for a selection of cell lines.

In some embodiments, computing system 802 is also configured to identify which cell lines should be subject to the procedures discussed above, i.e., which cell lines to use as "candidate" cell lines. For example, the computing system 802 (e.g. application 830 or another application) may analyze the results of cell count and diffusion assays (acquired by data collection unit 832 from analytical unit 852 of the cell line generation and analysis system 850) to determine which cell lines have the highest potential and should be advanced for further cell line development and screening. Cell lines that have both high cell productivity scores and high cell counts may be considered as the best candidates to achieve high performance at small-scale screening cultures. Identification of candidate cell lines may be performed automatically by processing unit 820, or by prediction unit 834, or in combination with a user manually weighing these factors via user input device 826. The identification may also be strictly manual, with a user evaluating the scores shown on display 824 and selecting which cell lines are to be candidates via user input device 826. FIG. 9 illustrates an example graphical output 860 of display 824 demonstrating a plot of cell counts versus cell productivity scores (Spotlight Assay Scores) for a selection of cell lines. Cell lines that a user may wish to select as candidate cell lines are encircled by a dashed line, for example. Various techniques for determining which models are best suited for predicting a given product quality attribute rankings for hypothetical small-scale screening cultures, and for identifying the most predictive features/inputs for a given model and/or product quality attribute, are now described with reference to FIGS. 10 through 12G.

Figure 10:
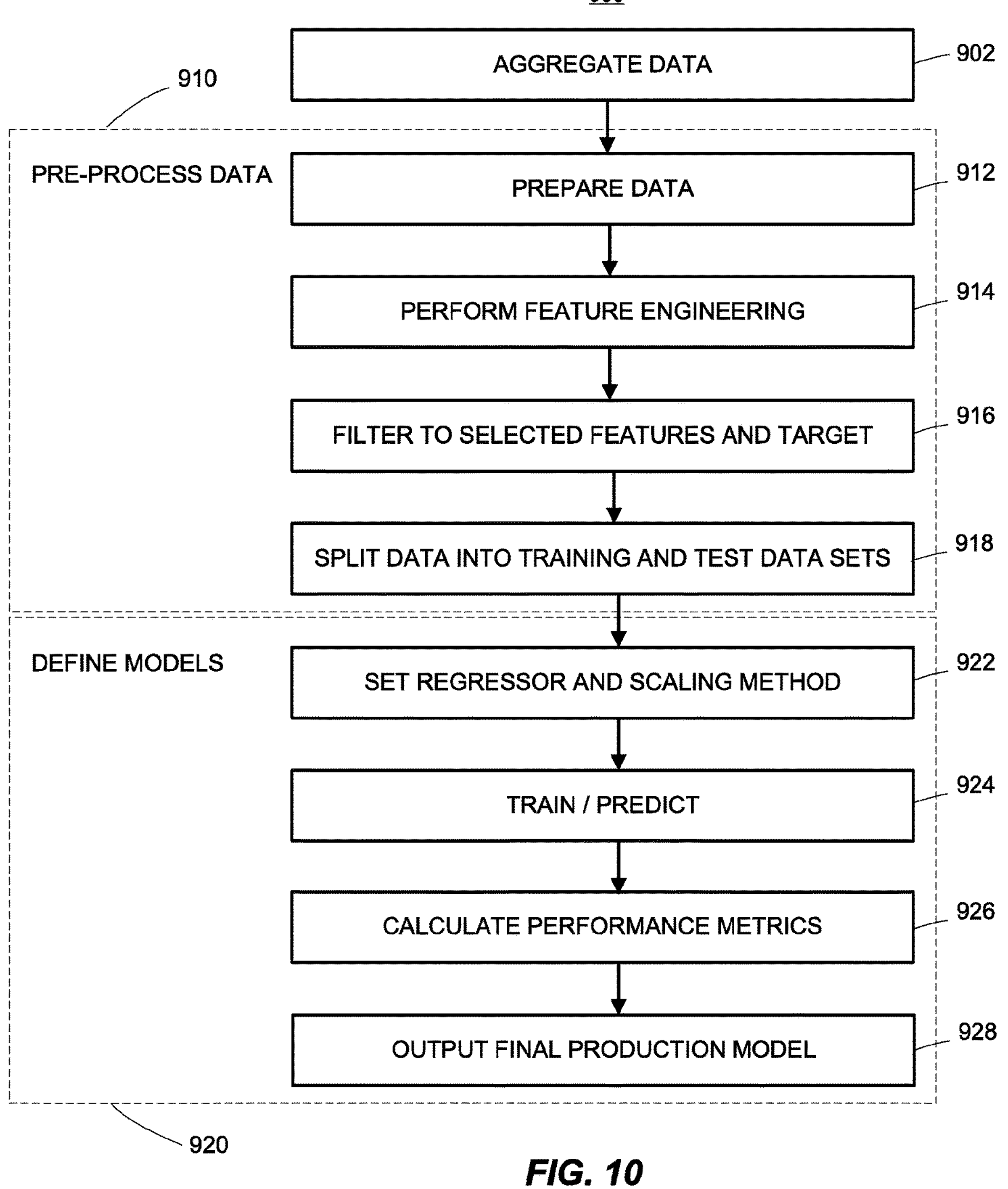
FIG. 10 depicts an example process for generating and evaluating machine learning models.

FIG. 10 illustrates an example of a modular, flexible process 900 that provides a data preparation and model selection framework. In particular, the process 900 can be used as a framework for identifying well-performing models for predicting values of different product quality attributes to facilitate the ranking of cell lines (e.g., by prediction unit 834) according to those attributes. At a high level, the process 900 includes a stage or step 902 for aggregating data, a stage 910 for data pre-processing, and a stage 920 for defining models. Generally, well-performing models for specific attribute values may be identified by training a number of different models using historical training data generated from previous cell line screening runs, and comparing the results. For example, an attribute may comprise cell growth and the machine learning model may comprise PLS; or an attribute may comprise specific productivity and the machine learning model may comprise PCA; or an attribute may comprise titer and the machine learning model may comprise a ridge regression model. Various measures may be taken to ensure a robust set of training data (e.g., providing standardized, heterogeneous data, removing outliers, imputing missing values, and so on). In some embodiments, special feature engineering techniques are used to extract or derive the best representations of the predictor variables to increase the effectiveness of the model. To avoid overfitting, in some embodiments, feature reduction may be performed. The models may be evaluated using metrics such as root mean square error (RMSE), to measure the accuracy of prediction values, and Spearman rho, to measure the correctness of the ranking order, for example.

At step 902, training server 804 receives data from training database 840 or any other suitable database. This step may include entering user input via user input device 826, with the user defining possible predictor variables and product quality attribute values to be predicted by the machine learning regression estimator (model). The predictor variables may include cell pool data, as well as data collected on a cell line generation and analysis system. While other embodiments may use other subcloning systems, the below discussion refers to an example in which Berkeley Lights' Beacon (abbreviated herein as "BLI") is used for the cell line generation and analysis system. The predicted variables may be defined as data collected during clone fedbatch experiments, for example. Initially, at step 902, relevant data is selected from among available historical data. Moreover, the historical data may include both categorical data, such as modality, and numerical data, such as cell counts and titer values. Cell pool data, for example, may include data on modality, VCD, pool viability, pool titer, pool specific productivity, and pool time integral VCD. Growth factors such as VCD and viability may be collected periodically over time (e.g., at different days of a 10-day culture). Cell line generation and growth data (BLI data), for example, may include data on cell productivity scores, BLI specific productivity, cell count, time integral VCD, doubling time, etc. Growth factors measured on BLI, such as cell count, may also be collected periodically over time (e.g., at different days after loading on a clone generation and growth unit such as unit 854). Small-scale culture (e.g., fedbatch culture) data that reflects the results when these cell lines were advanced to the next stage of cell line development (e.g., stage 12 of FIG. 1), such as titer, specific productivity, and/or cell growth measurement results, serve as the labels for the various feature sets. A non-limiting list of possible attributes/features, for both cell pool datasets (pool data), cell line generation and analysis datasets (BLI data), and fedbatch predictor variables is provided in Table 2 below.

In the example process 900, data pre-processing stage 910 includes steps 912 through 918. At step 912, training data is assessed and cleaned, including handling missing data and handling outliers. For example, missing records (e.g., pool VCD data for empty pens), zero values (e.g., values that were not recorded), incomplete data sets (e.g., for scenarios when data collection was not completed from cell pool to the end of fedbatch experiment for a cell line), outliers, and data from inconclusive experiments may be removed. In some embodiments, when using combined data sets, some data values may need to be adjusted to correct for instrument variability.

At step 914, in order to find the best representation of the predictor variables to increase the effectiveness of the model, special feature engineering techniques are used to extract or derive useful features from the dataset. Data may be visualized for the underlying relationships to determine which feature engineering steps should be assessed for performance improvement. For example, the best representation of the predictor variables may be (i) a transformation of a predictor, (ii) an interaction of two or more predictors such as a product or ratio, (iii) a functional relationship among predictors, or (iv) an equivalent re-representation of a predictor. The values for assay or growth may be scaled against cells of the same cohort to give an unbiased view of growth and assay score. From these observations, features may be calculated and added to the predictor dataset (e.g., cell count squared, pool titer squared, etc.).

Step 914 may include transforming categorical variables to numerical values. For example, for the categorical variable of modality, a monoclonal (mAb) modality may be transformed to "10," a particular bispecific modality may be transformed to "00," and so on. At data pre-processing step 916, the training data may be filtered to only include features selected in steps 912 and 914 above, and to defined targets/predictors (e.g., fedbatch titer, growth, and specific productivity).

When training and comparing machine learning models, k-fold cross validation can be used to measure model performance and select the optimal hyperparameters. Thus, at step 918, the training data may be split into training and test data sets for k-fold cross validation, to avoid training and testing on the same samples. For example, the number of folds can be defined by the number of subcloning projects used in the training data set (e.g., with k=6, where a model is trained and evaluated six times across different 5/1 partitions of the dataset).

Stage 920 defines machine learning models, and includes steps 922 through 928. At a high level, stage 920 may include setting a regressor and scaling method (step 922), training the predictive models (step 924) by running pre-processed data of stage 910 through each model in the model library over a range of hyperparameters, defining and calculating model performance metrics (step 926), and outputting a final production model (step 928).

Example step 922 populates a model library and sets the scaling method for each selected regression model. Preferably, some or all of the machine learning models selected for testing at step 922 will meet two criteria: (i) providing a quantitative output, and/or (ii) being interpretable (e.g., by providing coefficients weights or feature importance weights). Machine learning models that can assign weights to input features are generally preferred, as such models can explain the relative importance of each input feature with respect to predicting the target output. Sparsity-inducing machine learning models (e.g., models that initially accept many attribute values as features, but only require a small subset of those attribute values as features to make accurate predictions) are also generally preferred. This property mitigates over-fitting while also improving interpretability by excluding features that do not significantly affect the target result. Regression models/estimators based on decision trees (e.g., a random forest regression model, an eXtreme gradient boosting (xgboost) regression model), or other machine learning algorithm (e.g., a linear regression model, a ridge regression model, a lasso regression model, a principal component analysis (PCA) with linear regression model, or a partial least squares (PLS) regression model, etc.), can be particularly well-suited to satisfying both criteria noted above. While not traditionally viewed as being interpretable, one or more neural networks may also be selected at step 922, in some embodiments. Step 922 may also include setting a range of hyperparameters for the selected regression models.

Example step 924 trains the predictive models. For example, step 924 may train the models selected for inclusion in the library on the full set of feature data pre-processed in steps 912 and 914, for each target product quality attribute of interest and cross-validate across a range of hyperparameters defined in step 922. Step 924 may include performing k-fold validation for each model on data sets defined in step 918.

Example step 926 calculates performance metrics using the trained models. For each of k-fold splits, for example, algorithm performance metrics such as RMSE (for accuracy of predicting the target product quality attribute) and/or Spearman's rho (for ranking accuracy) may be calculated for each of the predictive models trained in step 924. Each trained model, with its tuned hyperparameters, is then evaluated using one of the folds as the test dataset, and the model with the best metric (e.g., highest Spearman's rho or lowest RMSE) for each predicted product quality attribute is chosen. The performance metrics of the iterative runs may be stored, and an average of the k folds (e.g., six folds) may be calculated to compare model performance. RMSE metric calculation is shown in Equation 2 above. Spearman's rho may be calculated as:

$$\rho = \frac{s_{xy}}{s_x s_y} = \frac{\frac{1}{n}\sum_{i=1}^{n}(R(x_i) - \overline{R(x)}) - (R(y_i - \overline{R(y)})}{\sqrt{\left(\frac{1}{n}\sum_{i=1}^{n}(R(x_i) - \overline{R(x)}))^2\right) \cdot \left(\frac{1}{n}\sum_{i=1}^{n}(R(y_i) - \overline{R(y)}))^2\right)}} \quad \text{(Equation 4)}$$

Counterintuitively, as noted above, the ability of certain machine learning models to correctly rank cell lines (according to the relative values of the product quality attributes predicted by the models) can far outperform the ability of those models to accurately predict product quality attributes. For instance, it has been found that certain machine learning models, while having relatively poor accuracy when predicting a value of a particular product quality attribute at the fedbatch stage, do a good job of predicting values in a relative sense (e.g., in terms of whether the predicted values are greater than or less than values that the model predicts for other cell lines). In the context of selecting cell lines to advance to a next stage of development, this ability to correctly rank cell lines can be sufficient, as it is generally more important to know which cell lines to advance to the next stage than it is to predict accurate and precise product quality attributes. Thus, Spearman's rho (rather than, for example, RMSE) may be the preferred metric to calculate at step 926.

Figures 11A, 11B:
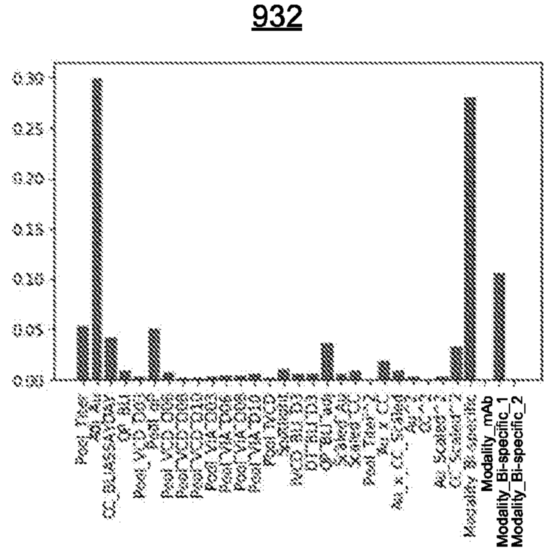
FIGS. 11A and 11B depict example outputs from a regression estimator that may be used for feature reduction.

At step 928, a "best" model is output/identified as the final production model based on the calculated metric(s) (e.g., the model having the highest Spearman's rho or lowest RMSE). If the best model is one that is interpretable, then step 928 may include determining the importance of each feature in making the prediction. For example, step 928 may include determining feature importance based on coefficients weights (e.g., generated by lasso regression models) or feature importance weights (e.g., generated by tree-based models such as xgboost). The output from these interpretable models (e.g., an indication of parameters shrunk by the lasso sparsity-inducing model, or feature importance plots showing how often each variable was split upon in training the tree of an xgboost model, etc.) may be analyzed by training server 804 or a human reviewer (via visualization unit 838) to determine the most predictive features (e.g., two to 10 features) for each relative ranking of candidate cell lines according to predicted product quality attribute values. For example, FIG. 11A is an example output 930 from a lasso regression model when predicting fedbatch titer, showing that pool titer is more predictive of fedbatch titer than cell productivity score (here, the "Spotlight" assay score), and cell productivity score is more predictive of fedbatch titer than cell count (which had no predictive power, or extremely little predictive power, for fedbatch titer). Similarly, FIG. 11B depicts an example feature importance plot 932 for an xgboost regression model predicting fedbatch titer, showing a strong feature importance for pool titer and cell productivity score (Adj_Au) relative to the other features used. The results show that the model should perform just as well without using a feature based on cell count (e.g., cell count squared or "$CC^2$"), for example. Thereafter, the winning/best model, or a new version of that model that has been trained using only the most predictive features, etc., may be used with a much smaller feature set. The model may then be stored as a trained model (e.g., by training server 804, in model(s) 808), and can be used to make predictions for new experiments (e.g., by prediction unit 834). Identifying highly predictive features may also be useful for other purposes, such as providing new scientific insights that may give rise to new hypotheses, which could in turn lead to bioprocess improvements.

Any suitable attributes may be used for the features discussed above (e.g., for initially training the various models, and possibly also for training the final production models, if the feature is of sufficient importance). A non-limiting list of possible attributes/features, for both cell pool datasets (pool data) and cell line generation and analysis datasets (BLI data), is provided in Table 2 below:

TABLE 2

| FEATURE | DATASET | DESCRIPTION |
|---|---|---|
| MODALITY | POOL | drug modality |
| MTX [mg] | POOL | methotrexate |
| POOL_VCD_D00 [e5 cells/ml] | POOL | pool viable cell density, day 00 |
| POOL_VCD_D03 [e5 cells/ml] | POOL | pool viable cell density, day 03 |
| POOL_VCD_D06 [e5 cells/ml] | POOL | pool viable cell density, day 06 |
| POOL_VCD_D08 [e5 cells/ml] | POOL | pool viable cell density, day 08 |
| POOL_VCD_D10 [e5 cells/ml] | POOL | pool viable cell density, day 10 |
| POOL_VIA_D00 [%] | POOL | pool viability, day 00 |
| POOL_VIA_D03 [%] | POOL | pool viability, day 03 |
| POOL_VIA_D06 [%] | POOL | pool viability, day 06 |
| POOL_VIA_D08 [%] | POOL | pool viability, day 08 |
| POOL_VIA_D10 [%] | POOL | pool viability, day 10 |
| POOL_TITER [g/L] | POOL | pool titer |
| POOL_IVCD | POOL | calculated value, pool time integral VCD |
| POOL_qP [μg/cell/day] | POOL | calculated value, pool specific productivity |
| SPOTLIGHT | BLI | cell productivity score |
| CC_BLIASSAYDAY | BLI | calculated value, cell count on day of assay on BLI |
| qP_BLI [μg/cell/day] | BLI | calculated value, specific productivity on BLI |
| CC_BLID1 | BLI | cell count, day 1 after loading on BLI |
| CC_BLID2 | BLI | cell count, day 2 after loading on BLI |
| CC_BLID3 | BLI | cell count, day 3 after loading on BLI |
| CC_BLID4 | BLI | cell count, day 4 after loading on BLI |
| CC_BLID5 | BLI | cell count, day 5 after loading on BLI |
| CC_BLID6 | BLI | cell count, day 6 after loading on BLI |
| IVCD_BLI_D3 | BLI | calculated value, time integral vcd, day 3 after loading on BLI |
| DT_BLI_D3 | BLI | calculated value, doubling time on BLI, day 3 |
| SCALED_Au | BLI | calculated value, scaled cell productivity score, captures the relative adj_Au score of a clone compared to others in the same cell line by scaling to the 25th/75th percentile scaling for that cell line only |
| Au_X_CC | BLI | calculated value, adjusted Au (cell productivity score) times cell count - captures the interaction of these two terms |
| SCALED_CC | BLI | calculated value, scaled cell count, captures the relative cell count of a clone compared to others in the same cell line by scaling to the 25th/75th percentile scaling for that cell line only |
| Au_X_CC_SCALED | BLI | calculated value, scaled Au score (cell productivity score) times scaled cell count - captures the interaction of these terms |
| CC^2 | BLI | calculated value, cell count squared |
| Au_SCALED^2 | BLI | calculated value, scaled Au score (cell productivity score) squared |
| CC_SCALED^2 | BLI | calculated value, scaled cell count squared |
| POOL_TITER^2 | POOL | calculated value, pool titer squared |
| Au^2 | BLI | calculated value, adjusted Au score (cell productivity score) squared |

FIG. 12A is a bar graph 934 depicting performance of the best model (output at step 928 of process 900) against baseline performance, using the Spearman's rho metric (here, across 6 folds of cross-validation) for the product quality attributes of cell growth, specific productivity, and titer. Each of the attributes was measured at the end-point of a small-scale cell culture process (here, day 10 of a fedbatch experiment). In this example, the specific productivity performance "baseline" is a linear regression in cell productivity score, with a higher cell productivity score corresponding to a higher predicted specific productivity. Similarly, the growth performance baseline is a linear regression in cell count, with a higher cell count corresponding to a higher predicted growth, and the titer performance baseline is a linear regression in cell productivity score and cell count, with higher scores in both corresponding to higher predicted titers.

As seen in FIG. 12A, the predictive power of the machine learning model identified/output at step 928 of process 900 (discussed further with reference to FIGS. 12B through 12G) surpasses the baseline performance for ranking candidate cell lines in all three target product quality attributes. The largest gain is seen in the model predicting growth rankings, where the model provided a rank correlation of $\rho=0.283$ as compared to the baseline $\rho=0$ (no predictive power). The model from step 928 showed only a small improvement in predicting specific productivity, with the rank correlation increasing from $\rho=0.468$ to the baseline $\rho=0.492$, which may mean that cell productivity score alone can account for most of the differences in specific productivity rank order. The model from step 928 provided a moderate increase in performance for predicting titer, with the rank correlation increasing from ρ=0.245 to ρ=0.342.

Different regression estimators of model library 922 have been found to be better suited to predict values of different target product quality attributes. Using the model identification/definition procedure outlined in stage 920, for example, the computing system 802 may test multiple regression estimators using the dataset defined in stage 910, and cross-validate each of the regression models across a range of hyperparameters. FIGS. 12B through 12G show examples of relative performance of different regression estimators in predicting particular performance attribute values, and the respective selected features used to build each model as chosen with the feature reduction method described herein with reference to step 928. The "best" performing regression estimator was selected as the model with the highest average Spearman's rho across all cell lines after optimizing the relevant hyperparameter (if any). While average RMSE is also shown in FIGS. 12B, 12D, and 12F, the metric was not used to select a model, for the reasons described elsewhere herein (i.e., due to the importance of relative/ranking accuracy over absolute accuracy).

As seen in a table 936 shown in FIG. 12B, the best regression estimator for predicting titer was found to be ridge regression with the hyperparameter lambda being equal to 1.3. This performance is closely followed by four other models: linear regression, lasso regression with lambda equal to 0.001, PCA with two principal components, and PLS with two principal components. Table 938 of FIG. 12B shows the two attributes analyzed by the models (pool titer and cell productivity score (Spotlight assay score)), which were selected with feature reduction.

Table 940 of FIG. 12D shows that the best predictor of specific productivity was PCA with two principle components. Table 942 of FIG. 12E shows the eight attributes analyzed by the models, which were selected with feature reduction. For the first PCA component, the values of pool titer, cell productivity score (Spotlight Assay Score), and specific productivity on the cell line generation and analysis system have more importance, while for the second PCA component the scaled values of these metrics (normalizing the different characteristics of each cell line) have more importance.

Table 944 of FIG. 12F shows that the best regression estimator for predicting growth was found to be PLS with one principle component. Table 946 of FIG. 12G shows the nine attributes analyzed by the models, which were selected with feature reduction. The models generally placed more weight on pool data than on data collected on the Berkeley Lights system. In particular, pool titer, pool IVCD, and pool Viable Cell Densities on Days 6 and 8 had the highest importance, while cell count had a lower weighting.

Figure 13A:
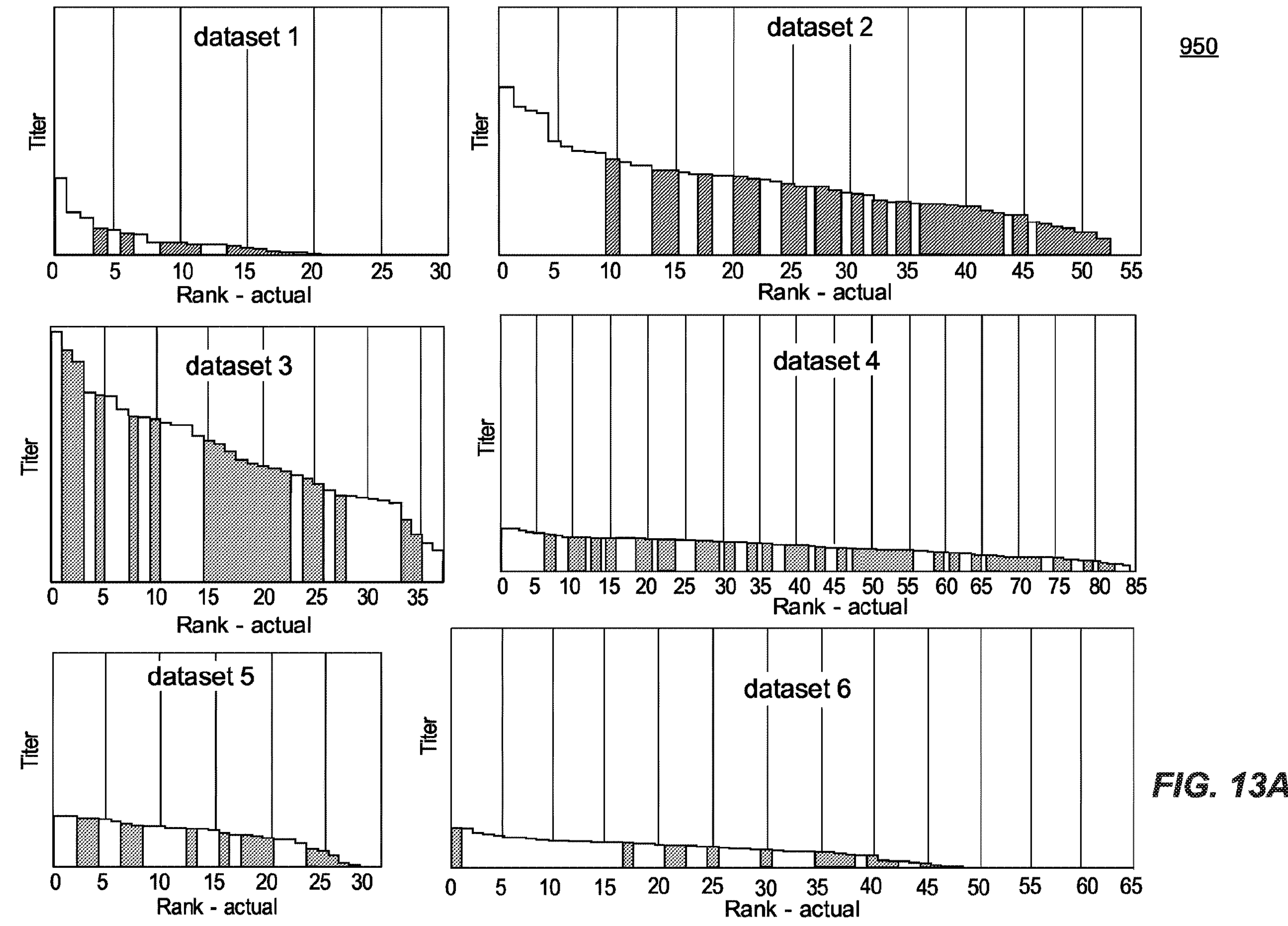
FIGS. 13A through 13C depict comparisons of model-predicted rankings with rankings based on real-world fed-batch cultures.
Figure 13B:
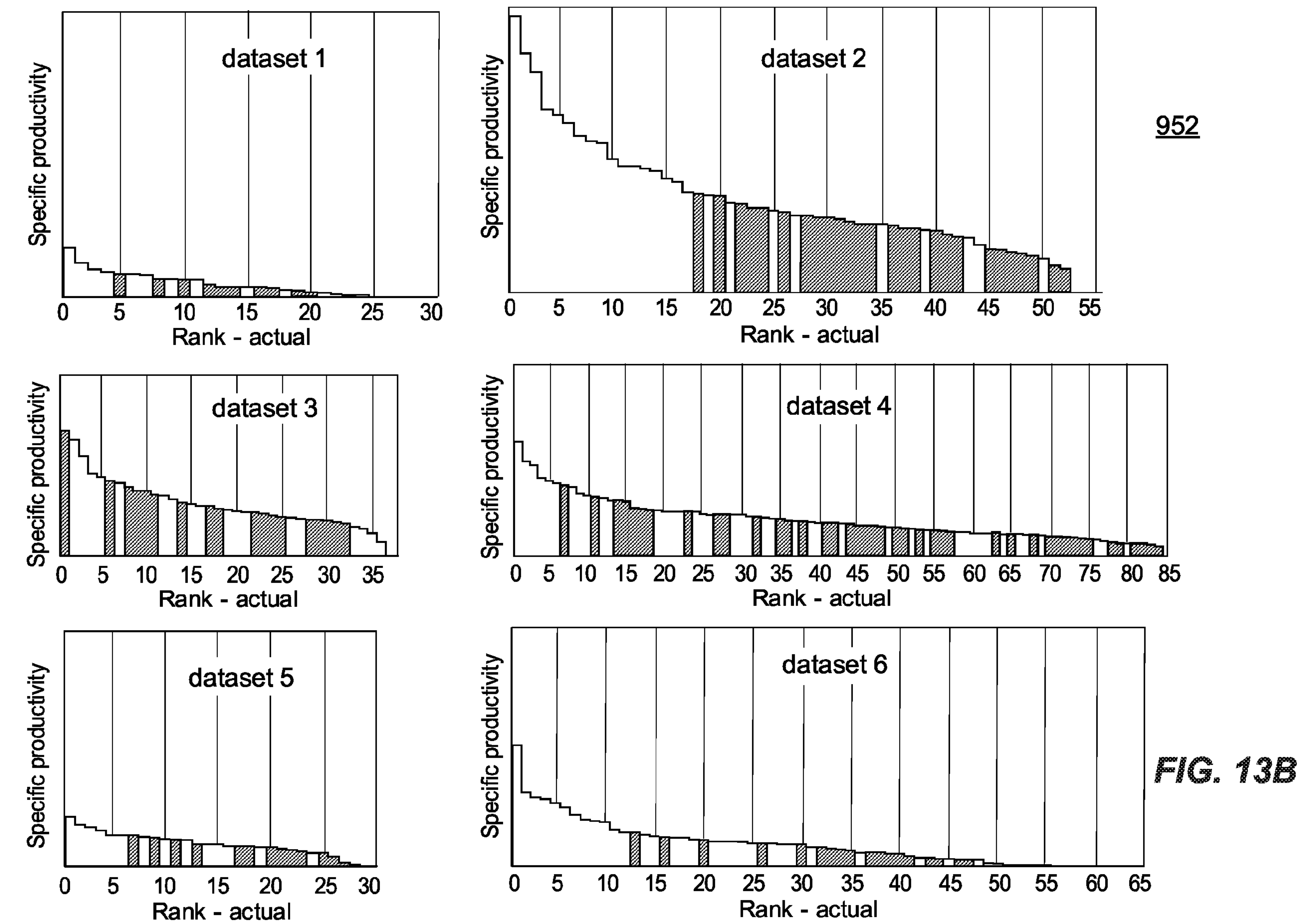
Figure 13C:
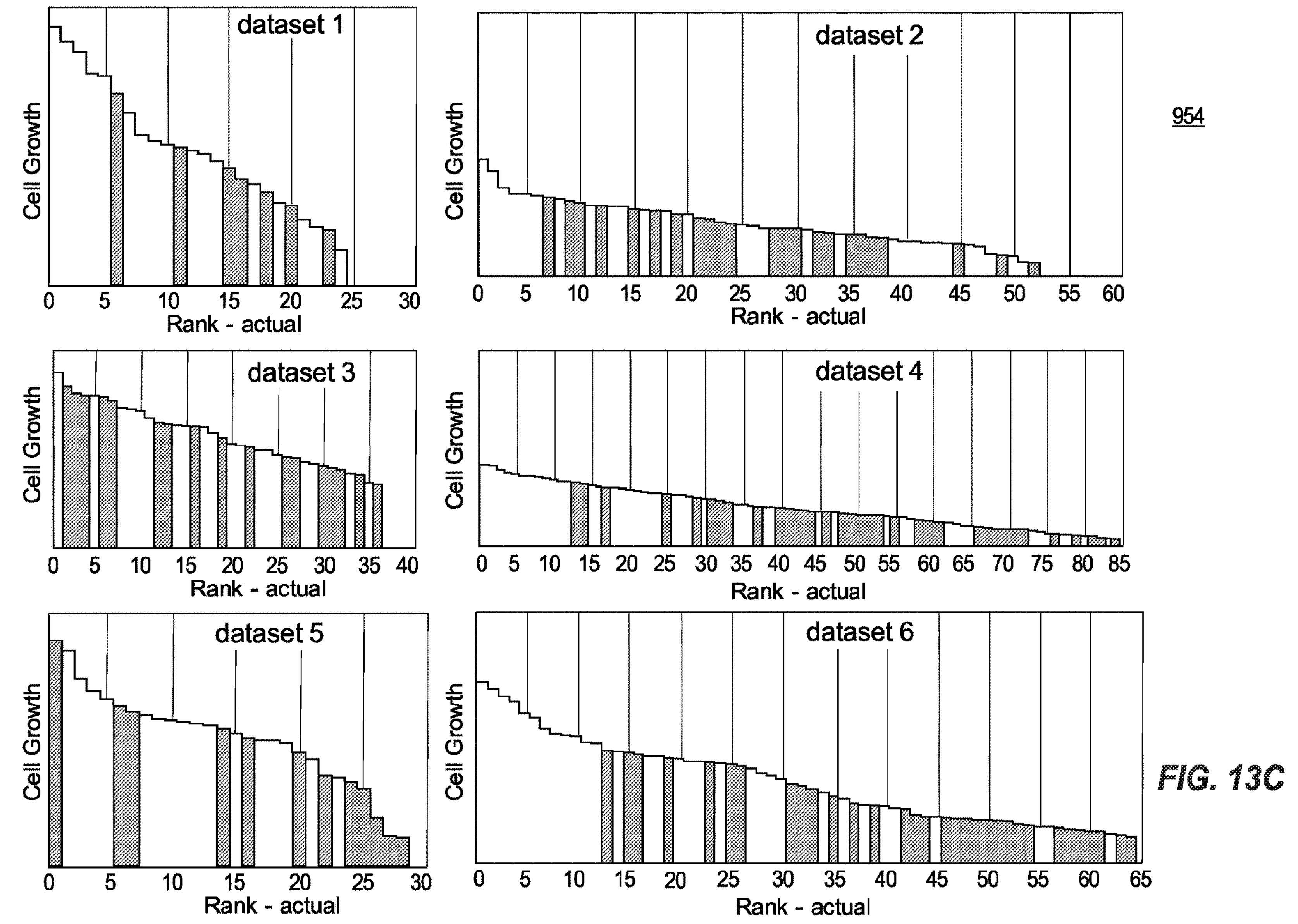

In addition to using Spearman's rho, other measures or visualizations may be used to determine the ranking accuracy of various models. Such an assessment may be expressed, for example, as a comparison between the rankings determined by the models and the actual ranks of the same cell lines in real-world fedbatch experiments. This assessment may also evaluate the ability of a model to capture the top cell lines (e.g., the top four cell lines) in a real-world fedbatch experiment for each target product attribute, e.g., by showing whether those top cell lines appear anywhere near the top (e.g., in the top 50%) of the cell lines as ranked by the model results. FIGS. 13A through 13C show example results of such an assessment. Each of FIGS. 13A through 13C shows six bar graphs, each representing assessment results for one of six evaluated datasets. The top 50% of the ranked cell lines are shown as white bars, and the bottom 50% of the ranked cell lines are shown as shaded bars. For a model that is perfectly predictive of ranking, a given bar graph would have all white bars located to the left (along the x-axis) of all of the shaded bars. The height of each bar represents the relative value of a product quality attribute as expressed in a real-world small-scale cell culture for each cell line.

Turning first to FIG. 13A, example results 950 correspond to predicted ranking of cell lines according to the product quality attribute of titer (in this example, titer measured on day 10 of a fedbatch, small-scale culture). As seen in FIG. 13A, a 50% reduction in exports (i.e., in cell lines advanced to the fedbatch stage) using the model would likely be too aggressive, and cause some of the top real-world cell lines to be excluded. In this example, to ensure all of the top four clones are selected, at least 38 clones would have to be exported from dataset 4.

FIG. 13B shows example results 952 that correspond to predicted ranking of cell lines according to the product quality attribute of specific productivity (in this example, specific productivity (qP) on day 10 of a fedbatch, small-scale culture). The model predictions of specific productivity were promising. For example, even halving the number of exports would only result in one of the top four clones being lost, across all cell lines. The maximum number of clones required (from the predicted rankings) to capture the top four clones was 31, and datasets 5 and 6 each identified all four top clones within the top eight clones predicted by the model.

FIG. 13B shows example results 954 that correspond to predicted ranking of cell lines according to the product quality attribute of cell growth (in this example, IVCD on day 10 of a fedbatch, small-scale culture). The model predictions of growth show that the best indicator is the pool from which the clone came, rather than growth on the cell line generation and growth unit. However, as demonstrated by datasets 3 and 5, the model did not predict some of the top-growing clones to be in the top 50%. This information is still valuable, however, when compared to the baseline of no predictive power of cell count (as measured at a cell line generation and growth unit). To ensure the top four clones were exported/advanced, a minimum of 37 clones would have to be exported based on the results from dataset 4.

Figure 1:
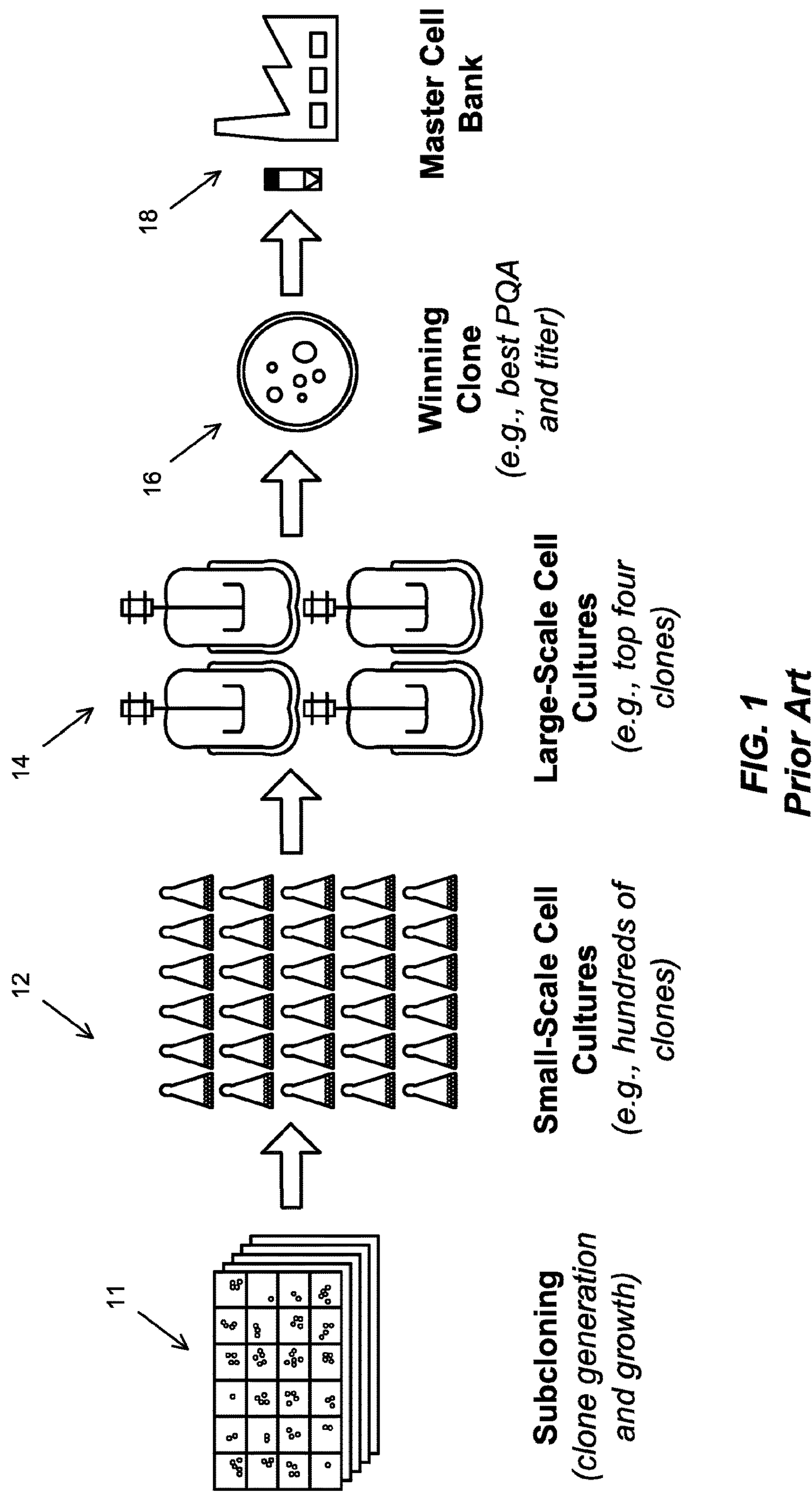
FIG. 1 depicts various stages of a typical clone screening process.
Figure 14:
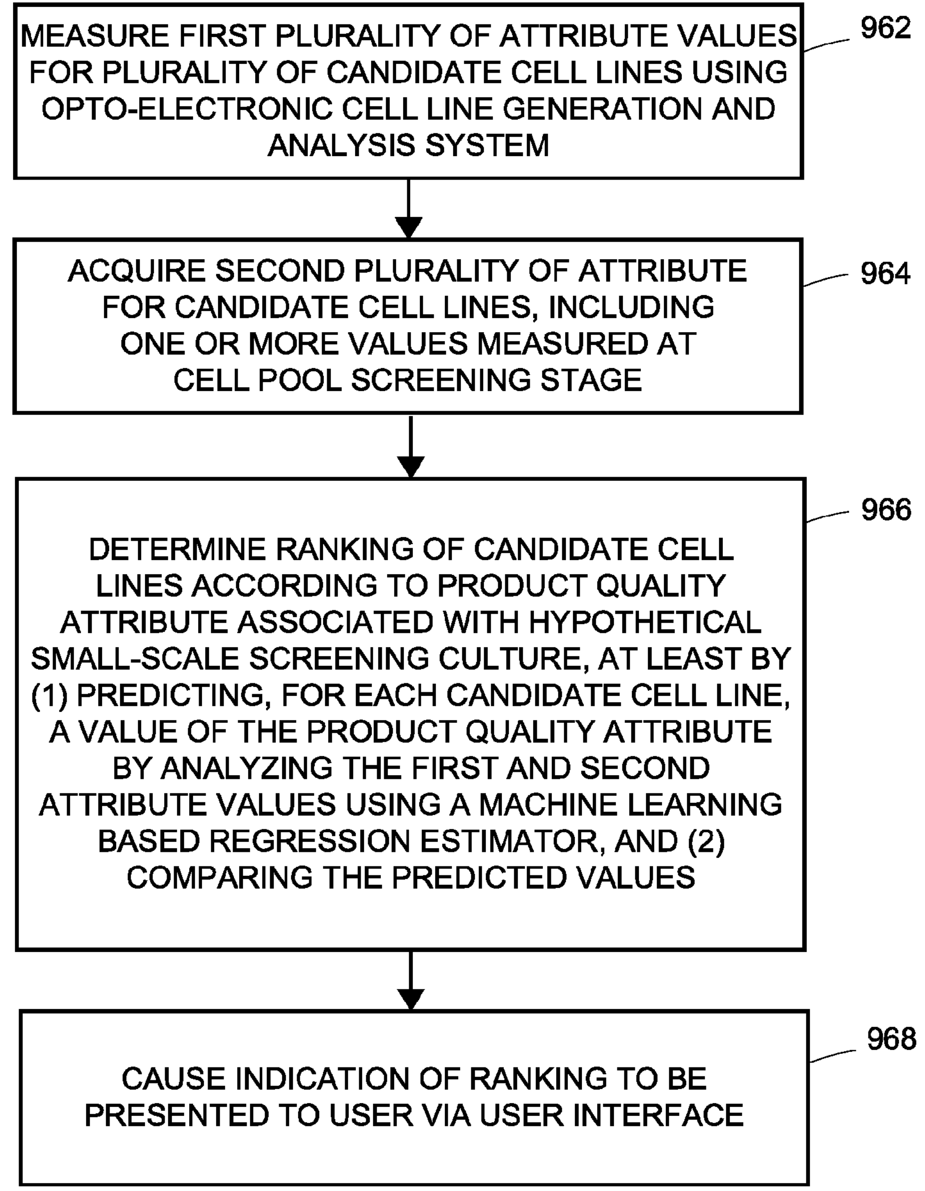
FIG. 14 is a flow diagram of an example method for facilitating selection of cell lines, from among a plurality of candidate cell lines that produce recombinant proteins, to advance to a next stage of cell line screening.

FIG. 14 is a flow diagram of an example method 960 for facilitating selection of cell lines from among candidate cell lines that produce recombinant proteins, to advance to a next stage of cell line screening (e.g., to stage 12 of FIG. 1). Some or all of method 960 may be implemented by processing unit 820 of computing system 802 when executing the software instructions of application 830 stored in memory unit 828, or by one or more processors of server 804 (e.g., in a cloud service implementation), for example.

At block 962, a first plurality of attribute values is measured for a plurality of candidate cell lines using an opto-electronic cell line generation and analysis system (e.g., system 850 of FIG. 2). The opto-electronic cell line generation and analysis system may perform optical and assay measurements for the candidate cell lines at block 962, for example. In some embodiments, such measurements are performed, at least in part, by measuring at least cell counts and cell productivity scores at a plurality of physically isolated pens in the opto-electronic cell line generation and analysis system. In some of these embodiments, block 962 further includes generating cells of the candidate cell lines using the opto-electronic cell line generation and analysis system, at least by moving individual cells into different ones of the physically isolated pens with one or more photoconductors activated by light patterns, and by containing the individual cells within their respective pens throughout a cell line generation and analysis process. Further still, block 962 may include measuring different values of the first plurality of attribute values on different days of the cell line generation and analysis process. More generally, the first plurality of attribute values may include values of any of the attributes that can be measured by analytical unit 852 as discussed elsewhere herein, and/or may include values of any suitable attributes that can be measured using an opto-electronic cell line generation and analysis system.

At block 964, a second plurality of attribute values for the candidate cell lines is acquired. The second plurality of attribute values includes one or more attribute values measured at a cell pool screening stage of the candidate cell lines. Attribute values measured at block 964 may include, for example, pool titer, VCD, and/or pool viability. In some embodiments and/or scenarios, other attribute values are instead, or also, acquired at block 964, such as values that are computed based on one or more direct measurements (e.g., time integral VCD, pool specific productivity, etc.), or values that a device other than the measuring device (e.g., computing system 802) computes based on one or more direct measurements, and/or user-entered values (e.g., modality). In some embodiments, some of the attribute values acquired at block 964 are measurements obtained periodically over time (e.g., at different days). For example, a first attribute value may be a VCD value at Day 0 for a cell pool, and a second attribute value may be a VCD value at Day 3 for the same cell pool, and so on. More generally, the second plurality of attribute values may include values of any of the attributes that can be measured by analytical instrument(s) 812 or are otherwise associated with cell pool(s) 810 as discussed elsewhere herein, and/or may include values of other suitable attributes that can be associated with a cell pool.

At block 966, a ranking of the candidate cell lines, according to a product quality attribute associated with hypothetical small-scale screening cultures for the candidate cell lines, is determined. Block 966 includes predicting a value of the product quality attribute for each of the candidate cell lines, by analyzing the first plurality of attribute values measured at block 962 and the second plurality of attribute values acquired at block 964 using a machine learning based regression estimator. Block 968 also includes comparing the predicted values, i.e., to rank the candidate cell lines (e.g., in order from best to worst with respect to the predicted values). In some embodiments, the predicted value is a predicted value of a cell growth metric. In other embodiments, the predicted value is a titer, a specific productivity metric, or any other suitable indicator of performance at the hypothetical small-scale culture screening stage. The machine learning based regression estimator may be any suitable type of regression estimator (e.g., ridge, lasso, PCA, PCS, xgboost, etc.). In other embodiments, other types of machine learning models may be used (e.g., by prediction unit 834) to make the prediction at block 966 (e.g., a neural network, etc.).

In some embodiments, block 966 includes determining the ranking according to titer, at least by (i) predicting, for each of the plurality of candidate cell lines, a titer by analyzing the first plurality of attribute values and the second plurality of attribute values using the machine learning based regression estimator, and (ii) comparing the predicted titers. In some of these embodiments, the first plurality of attribute values includes a value based on a cell productivity score (e.g., the score itself, or a value derived from that score), and/or the second plurality of attribute values includes a value based on a cell pool titer (e.g., the cell pool titer itself, or a value derived from that score). The machine learning based regression estimator that analyzes these attributes may be a ridge regression estimator, for example.

In other embodiments, block 966 includes determining the ranking according to specific productivity, at least by (i) predicting, for each of the plurality of candidate cell lines, a specific productivity metric by analyzing the first plurality of attribute values and the second plurality of attribute values using the machine learning based regression estimator, and (ii) comparing the predicted specific productivity metrics. In some of these embodiments, the first plurality of attribute values includes a value based on a cell productivity score and a value based on cell count, and/or the second plurality of attribute values includes a value based on a cell pool titer. The machine learning based regression estimator that analyzes these attributes may be a PCA regression estimator with two principal components, for example.

In still other embodiments, block 966 includes determining the ranking according to cell growth, at least by (i) predicting, for each of the plurality of candidate cell lines, a cell growth metric by analyzing the first plurality of attribute values and the second plurality of attribute values using the machine learning based regression estimator, and (ii) comparing the predicted cell growth metrics. In some of these embodiments, the first plurality of attribute values includes a value based on cell count, and the second plurality of attribute values includes a value based on cell pool time integral viable cell density (iVCD), a value based on cell pool viable cell densities (VCD) at different days, and a value based on cell pool viability at different days. The machine learning based regression estimator that analyzes these attributes may be a PLS regression estimator with one principal component, for example.

At block 968, an indication of the ranking (e.g., an ordered list, bar graph, etc.) is caused to be presented to a user via a user interface. For example, block 968 may include generating or populating (e.g., by visualization unit 838) a GUI, and causing the GUI to be presented on a display (e.g., display 824). In some embodiments, the presentation of the indication is caused by sending data indicative of the ranking to another computing device or system, which uses the data to populate and present a GUI.

In some embodiments, method 960 includes one or more additional blocks not shown in FIG. 14. For example, method 960 may include an additional block (e.g., prior to block 962) in which performance of the machine learning based regression estimator is evaluated at least by calculating an average Spearman's rank correlation coefficient for the machine learning based regression estimator (e.g., as calculated according to Equation 4). As another example, method 960 may include an additional block in which, based on the ranking determined at block 966, one or more cell lines of the candidate cell lines is/are advanced to the next stage of cell line screening (e.g., a fedbatch cell culture stage).

Aspects of the present invention may include:

Aspect 1. A method for facilitating selection of a cell line, from among a plurality of candidate cell lines that produce recombinant proteins, the method comprising: measuring, using an opto-electronic cell line generation and analysis system, a first plurality of attribute values for the plurality of candidate cell lines; acquiring, by one or more processors, a second plurality of attribute values for the plurality of candidate cell lines, wherein the second plurality of attribute values includes one or more attribute values measured at a cell pool screening stage of the plurality of candidate cell lines; determining, by one or more processors, a ranking of the plurality of candidate cell lines according to a product quality attribute associated with hypothetical small-scale screening cultures for the plurality of candidate cell lines, wherein determining the ranking includes (i) predicting, for each of the plurality of candidate cell lines, a value of the product quality attribute by analyzing the first plurality of attribute values and the second plurality of attribute values using a machine learning based regression estimator, and (ii) comparing the predicted values; and causing an indication of the ranking to be presented to a user via a user interface.

Aspect 2. The method of aspect 1, wherein measuring the first plurality of attribute values using the opto-electronic cell line generation and analysis system includes performing a plurality of optical and assay measurements for the plurality of candidate cell lines.

Aspect 3. The method of aspect 2, wherein performing the plurality of optical and assay measurements for the plurality of candidate cell lines includes measuring at least cell counts and cell productivity scores at a plurality of physically isolated pens in the opto-electronic cell line generation and analysis system, and wherein the method further comprises: generating, using the opto-electronic cell line generation and analysis system, cells of the plurality of candidate cell lines, at least by moving individual cells into different pens of the plurality of physically isolated pens with one or more photoconductors activated by light patterns, and containing the individual cells within their respective pens throughout a cell line generation and analysis process.

Aspect 4. The method of aspect 3, wherein measuring the first plurality of attribute values includes measuring: a first attribute value corresponding to a first measurement of an attribute; and a second attribute value corresponding to a second measurement of the attribute, the first measurement and the second measurement occurring on different days of the cell line generation and analysis process.

Aspect 5. The method of any one of aspects 1 through 4, wherein acquiring the second plurality of attribute values includes receiving one or more of: a measured cell pool titer; a measured cell pool viable cell density (VCD); or a measured cell pool viability.

Aspect 6. The method of any one of aspects 1 through 5, wherein acquiring the second plurality of attribute values includes receiving attribute values measured on different days of the cell pool screening stage.

Aspect 7. The method of any one of aspects 1 through 6, wherein the one or more product quality attributes include a cell growth metric.

Aspect 8. The method of any one of aspects 1 through 6, wherein the one or more product quality attributes include one or more of (i) a titer or (ii) a specific productivity metric.

Aspect 9. The method of any one of aspects 1 through 8, wherein: determining the ranking includes determining the ranking according to titer, at least by (i) predicting, for each of the plurality of candidate cell lines, a titer by analyzing the first plurality of attribute values and the second plurality of attribute values using the machine learning based regression estimator, and (ii) comparing the predicted titers; the first plurality of attribute values includes a value based on a cell productivity score; and the second plurality of attribute values includes a value based on a cell pool titer.

Aspect 10. The method of aspect 9, wherein predicting the titer includes analyzing the first plurality of attribute values using a Ridge regression estimator.

Aspect 11. The method of any one of aspects 1 through 8, wherein: determining the ranking includes determining the ranking according to specific productivity, at least by (i) predicting, for each of the plurality of candidate cell lines, a specific productivity metric by analyzing the first plurality of attribute values and the second plurality of attribute values using the machine learning based regression estimator, and (ii) comparing the predicted specific productivity metrics; the first plurality of attribute values includes a value based on a cell productivity score and a value based on cell count; and the second plurality of attribute values includes a value based on cell pool titer.

Aspect 12. The method of aspect 11, wherein predicting the specific productivity metric includes using a Principal Component Analysis (PCA) regression estimator with two principal components.

Aspect 13. The method of any one of aspects 1 through 8, wherein: determining the ranking includes determining the ranking according to cell growth, at least by (i) predicting, for each of the plurality of candidate cell lines, a cell growth metric by analyzing the first plurality of attribute values and the second plurality of attribute values using the machine learning based regression estimator, and (ii) comparing the predicted cell growth metrics; the first plurality of attribute values includes a value based on cell count; and the second plurality of attribute values includes a value based on cell pool titer, a value based on cell pool time integral viable cell density (iVCD), a value based on cell pool viable cell densities (VCD) at different days, and a value based on cell pool viability at different days.

Aspect 14. The method of aspect 13, wherein predicting the cell growth metric includes using a Partial Least Squares (PLS) regression estimator with one principal component.

Aspect 15. The method of any one of aspects 1 through 14, wherein the method further comprises evaluating performance of the machine learning based regression estimator at least by calculating a Spearman's rho or average Spearman's rho for the machine learning based regression estimator.

Aspect 16. The method of any one of aspects 1 through 15, wherein the method further comprises: based on the ranking, advancing one or more cell lines of the plurality of candidate cell lines to a next stage of cell line screening.

Aspect 17. The method of aspect 16, wherein the next stage of cell line screening is a fedbatch cell culture stage.

Aspect 18. One or more non-transitory, computer-readable media storing instructions that, when executed by one or more processors of a computing system, cause the computing system to perform the method of any one of aspects 1 through 15.

Aspect 19. A computing system comprising: one or more processors; and one or more non-transitory, computer-readable media storing instructions that, when executed by the one or more processors, cause the computing system to perform the method of any one of aspects 1 through 15.

Aspect 20. A method for facilitating selection of a master cell line from among candidate cell lines that produce recombinant proteins, the method comprising: receiving, by one or more processors of a computing system, a plurality of attribute values associated with a small-scale cell culture for a specific cell line, wherein at least some of the plurality of attribute values are measurements of the small-scale cell culture; predicting, by the one or more processors, one or more attribute values associated with a hypothetical large-scale cell culture for the specific cell line, at least by analyzing the plurality of attribute values associated with the small-scale cell culture using a machine learning based regression estimator, wherein the predicted one or more attribute values include a titer and/or one or more product quality attribute values; and causing, by the one or more processors, one or both of (i) the predicted one or more attribute values, and (ii) an indication of whether the predicted one or more attribute values satisfy one or more cell line selection criteria, to be presented to a user via a user interface to facilitate selection of the master cell line for use in drug product manufacturing.

Aspect 21. The method of aspect 20, wherein analyzing the plurality of attribute values using a machine learning based regression estimator includes analyzing the plurality of attribute values using a decision tree regression estimator.

Aspect 22. The method of aspect 21, wherein analyzing the plurality of attribute values using a machine learning based regression estimator includes analyzing the plurality of attribute values using a random forest regression estimator.

Aspect 23. The method of aspect 21, wherein analyzing the plurality of attribute values using a machine learning based regression estimator includes analyzing the plurality of attribute values using an xgboost regression estimator.

Aspect 24. The method of aspect 20, wherein analyzing the plurality of attribute values using a machine learning based regression estimator includes analyzing the plurality of attribute values using a linear support vector machine (SVM) regression estimator.

Aspect 25. The method of aspect 20, wherein analyzing the plurality of attribute values using a machine learning based regression estimator includes analyzing the plurality of attribute values using an elastic net estimator.

Aspect 26. The method of any one of aspects 20 through 25, wherein the predicted one or more attribute values include the one or more product quality attributes.

Aspect 27. The method of aspect 26, wherein the predicted one or more product quality attribute values includes one or more predicted chromatography measurements.

Aspect 28. The method of any one of aspects 20 through 27, further comprising: receiving, from a user via a user interface, user-entered data including one or more of: an identifier of the specific cell line, a modality of a drug to be produced using the specific cell line, an indication of the drug product to be produced using the specific cell line, or a protein scaffold type associated with the drug to be produced using the specific cell line, wherein analyzing the plurality of attribute values associated with the small-scale cell culture using the machine learning based regression estimator further includes analyzing the user-entered data using the machine learning based regression estimator.

Aspect 29. The method of any one of aspects 20 through 28, wherein receiving the plurality of attribute values associated with the small-scale cell culture includes receiving one or more of: a measured titer of the small-scale cell culture; a measured viable cell density of the small-scale cell culture; or a measured viability of the small-scale cell culture.

Aspect 30. The method of any one of aspects 20 through 29, wherein receiving the plurality of attribute values associated with the small-scale cell culture includes receiving one or more characteristics of a media of the small-scale cell culture.

Aspect 31. The method of aspect 30, wherein receiving the one or more characteristics of the media includes receiving a measured glucose concentration of the media.

Aspect 32. The method of any one of aspects 20 through 31, wherein receiving the plurality of attribute values associated with the small-scale cell culture includes receiving: a first attribute value corresponding to a first measurement of an attribute associated with the small-scale cell culture; and a second attribute value corresponding to a second measurement of the attribute associated with the small-scale cell culture, the first measurement and the second measurement occurring on different days of the small-scale cell culture.

Aspect 33. The method of any one of aspects 20 through 32, further comprising, prior to receiving the plurality of attribute values associated with the small-scale cell culture: receiving, by the one or more processors and from a user via a user interface, data indicative of a use case; and selecting, by the one or more processors and based on the data indicative of the use case, the machine learning based regression estimator from among a plurality of estimators, each of the plurality of estimators being designed for a different use case.

Aspect 34. The method of aspect 33, wherein receiving data indicative of the use case includes receiving data indicative of at least (i) at least one of the one or more attribute values associated with the hypothetical large-scale cell culture, and (ii) a modality of a drug to be produced.

Aspect 35. The method of aspect 34, wherein: receiving data indicative of the use case includes receiving data indicative of at least a titer associated with the hypothetical large-scale cell culture; and analyzing the plurality of attribute values using a machine learning based regression estimator includes analyzing the plurality of attribute values using (i) a decision tree regression estimator, (ii) a random forest regression estimator, (iii) an xgboost regression estimator, or (iv) a linear support vector machine (SVM) regression estimator.

Aspect 36. The method of aspect 34, wherein: receiving data indicative of the use case includes receiving data indicative of at least a chromatography measurement that is associated with the hypothetical large-scale cell culture; and analyzing the plurality of attribute values using a machine learning based regression estimator includes analyzing the plurality of attribute values using an xgboost regression estimator.

Aspect 37. The method of aspect 33, wherein: the method further comprises, for each estimator of the plurality of estimators, determining, by the one or more processors, a set of features most predictive of an output of the estimator; and receiving the plurality of attribute values associated with the small-scale cell culture includes receiving only attribute values that are included within the set of features determined for the machine learning based regression estimator.

Aspect 38. The method of any one of aspects 20 through 37, further comprising: measuring, by one or more analytical instruments, the at least some of the plurality of attribute values associated with the small-scale cell culture.

Aspect 39. The method of any one of aspects 20 through 38, wherein receiving the plurality of attribute values comprises receiving measurements from an opto-electronic cell line generation and analysis system.

Aspect 40. One or more non-transitory, computer-readable media storing instructions that, when executed by one or more processors of a computing system, cause the computing system to perform the method of any one of aspects 20 through 39.

Aspect 41. A computing system comprising: one or more processors; and one or more non-transitory, computer-readable media storing instructions that, when executed by the one or more processors, cause the computing system to perform the method of any one of aspects 20 through 39.

Although the systems, methods, devices, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method for facilitating selection of a cell line, from among a plurality of candidate cell lines that produce recombinant proteins, the method comprising:

measuring, using an opto-electronic cell line generation and analysis system comprising an analytical unit and a cell line generation and growth unit, a first plurality of attribute values for the plurality of candidate cell lines by performing a plurality of optical and assay measurements for the plurality of candidate cell lines, wherein performing the plurality of optical and assay measurements for the plurality of candidate cell lines includes measuring, using the analytical unit, at least cell counts and cell productivity scores at a plurality of physically isolated pens in the opto-electronic cell line generation and analysis system;

generating, using the opto-electronic cell line generation and analysis system, cells of the plurality of candidate cell lines, at least by moving individual cells into different pens of the plurality of physically isolated pens with one or more photoconductors activated by light patterns, wherein the individual cells are maintained within their respective pens throughout a cell line generation and analysis process;

acquiring, by one or more processors, a second plurality of attribute values for the plurality of candidate cell lines, wherein the second plurality of attribute values includes one or more attribute values measured at a cell pool screening stage of the plurality of candidate cell lines;

determining, by one or more processors, a ranking of the plurality of candidate cell lines according to a product quality attribute associated with hypothetical small-scale screening cultures for the plurality of candidate cell lines, wherein determining the ranking includes (i) predicting, for each of the plurality of candidate cell lines, a value of the product quality attribute by analyzing the first plurality of attribute values and the second plurality of attribute values using a machine learning based regression estimator, and (ii) comparing the predicted values; and causing an indication of the ranking to be presented to a user via a user interface.

2. The method of claim 1, wherein measuring the first plurality of attribute values includes measuring:

a first attribute value corresponding to a first measurement of an attribute; and a second attribute value corresponding to a second measurement of the attribute, the first measurement and the second measurement occurring on different days of the cell line generation and analysis process.

3. The method of claim 1, wherein acquiring the second plurality of attribute values includes receiving one or more of:

a measured cell pool titer;

a measured cell pool viable cell density (VCD); or a measured cell pool viability.

4. The method of claim 1, wherein acquiring the second plurality of attribute values includes receiving attribute values measured on different days of the cell pool screening stage.

5. The method of claim 1, wherein the one or more product quality attributes include a cell growth metric.

6. The method of claim 1, wherein the one or more product quality attributes include one or more of (i) a titer or (ii) a specific productivity metric.

7. The method of claim 1, wherein:

determining the ranking includes determining the ranking according to titer, at least by (i) predicting, for each of the plurality of candidate cell lines, a titer by analyzing the first plurality of attribute values and the second plurality of attribute values using the machine learning based regression estimator, and (ii) comparing the predicted titers;

the first plurality of attribute values includes a value based on a cell productivity score; and the second plurality of attribute values includes a value based on a cell pool titer.

8. The method of claim 7, wherein predicting the titer includes analyzing the first plurality of attribute values using a Ridge regression estimator.

9. The method of claim 1, wherein:

determining the ranking includes determining the ranking according to specific productivity, at least by (i) predicting, for each of the plurality of candidate cell lines, a specific productivity metric by analyzing the first plurality of attribute values and the second plurality of attribute values using the machine learning based regression estimator, and (ii) comparing the predicted specific productivity metrics;

the first plurality of attribute values includes a value based on a cell productivity score and a value based on cell count; and the second plurality of attribute values includes a value based on cell pool titer.

10. The method of claim 9, wherein predicting the specific productivity metric includes using a Principal Component Analysis (PCA) regression estimator with two principal components.

11. The method of claim 1, wherein:

determining the ranking includes determining the ranking according to cell growth, at least by (i) predicting, for each of the plurality of candidate cell lines, a cell growth metric by analyzing the first plurality of attribute values and the second plurality of attribute values using the machine learning based regression estimator, and (ii) comparing the predicted cell growth metrics;

the first plurality of attribute values includes a value based on cell count; and the second plurality of attribute values includes a value based on cell pool titer, a value based on cell pool time integral viable cell density (iVCD), a value based on cell pool viable cell densities (VCD) at different days, and a value based on cell pool viability at different days.

12. The method of claim 11, wherein predicting the cell growth metric includes using a Partial Least Squares (PLS) regression estimator with one principal component.

13. The method of claim 1, wherein the method further comprises evaluating performance of the machine learning based regression estimator at least by calculating a Spearman's rho or average Spearman's rho for the machine learning based regression estimator.

14. The method of claim 1, wherein the method further comprises:

based on the ranking, advancing one or more cell lines of the plurality of candidate cell lines to a next stage of cell line screening.

15. The method of claim 14, wherein the next stage of cell line screening is a fedbatch cell culture stage.

16. A method for facilitating selection of a master cell line from among candidate cell lines that produce recombinant proteins, the method comprising:

receiving, by one or more processors of a computing system, a plurality of attribute values associated with a small-scale cell culture for a specific cell line, wherein at least some of the plurality of attribute values are measurements of the small-scale cell culture captured by performing a plurality of optical and assay measurements for the plurality of candidate cell lines, the plurality of optical and assay measurements for the plurality of candidate cell lines include at least measured cell counts and measured cell productivity scores at a plurality of physically isolated pens of an opto-electronic cell line generation and analysis system, wherein performing the plurality of optical and assay measurements includes using the opto-electronic cell line generation and analysis system to (i) generate cells of the plurality of candidate cell lines, at least by moving individual cells into different pens of the plurality of physically isolated pens with one or more photoconductors activated by light patterns, and (ii) maintain the individual cells within their respective pens throughout a cell line generation and analysis process;

predicting, by the one or more processors, one or more attribute values associated with a hypothetical large-scale cell culture for the specific cell line, at least by analyzing the plurality of attribute values associated with the small-scale cell culture using a machine learning based regression estimator, wherein the predicted one or more attribute values include a titer and/or one or more product quality attribute values; and causing, by the one or more processors, one or both of (i) the predicted one or more attribute values, and (ii) an indication of whether the predicted one or more attribute values satisfy one or more cell line selection criteria, to be presented to a user via a user interface to facilitate selection of the master cell line for use in drug product manufacturing.

* * * * *